US012005244B2

United States Patent
Moleda et al.

(10) Patent No.: US 12,005,244 B2
(45) Date of Patent: Jun. 11, 2024

(54) NEEDLE-BASED DEVICE BASED ON DIRECT WING-BASED COUPLING OF A NEEDLE SHIELD TO A BARREL THEREOF AND SAFETY MECHANISM IMPLEMENTED THEREIN

(71) Applicants: Jaroslaw Moleda, Warsaw (PL); Maciej Zurawicz, Łódź (PL); Robert Grzelak, Warsaw (PL)

(72) Inventors: Jaroslaw Moleda, Warsaw (PL); Maciej Zurawicz, Łódź (PL); Robert Grzelak, Warsaw (PL)

(73) Assignee: MEDIVENA SP. Z O.O., Warsaw (PL)

( * ) Notice: Subject to any disclaimer, the term of this patent is extended or adjusted under 35 U.S.C. 154(b) by 0 days.

(21) Appl. No.: 18/221,848

(22) Filed: Jul. 13, 2023

(65) Prior Publication Data
US 2023/0355889 A1 Nov. 9, 2023

Related U.S. Application Data

(63) Continuation-in-part of application No. 17/494,904, filed on Oct. 6, 2021, now Pat. No. 11,786,672, and
(Continued)

(51) Int. Cl.
*A61M 5/32* (2006.01)
*A61M 5/31* (2006.01)
(Continued)

(52) U.S. Cl.
CPC ........ *A61M 5/3202* (2013.01); *A61M 5/3129* (2013.01); *A61M 5/3148* (2013.01);
(Continued)

(58) Field of Classification Search
CPC .... A61M 5/3243–3275; A61M 5/3234; A61M 5/3213; A61M 5/3202; A61M 5/32;
(Continued)

(56) References Cited

U.S. PATENT DOCUMENTS

| 3,381,686 A | * | 5/1968 | Pierce | ............... A61M 5/34 264/249 |
| 4,425,120 A | | 1/1984 | Sampson et al. | |

(Continued)

FOREIGN PATENT DOCUMENTS

| EP | 1317938 B1 | 7/2006 |
| EP | 1949929 B1 | 11/2009 |

(Continued)

OTHER PUBLICATIONS

"Insulin Safety Syringes" by Medivena, Found Online on [May 31, 2021] https://www.one-care.com/safety-insulin-syringes.
(Continued)

*Primary Examiner* — Chelsea E Stinson
*Assistant Examiner* — Hong-Van N Trinh
(74) *Attorney, Agent, or Firm* — LEGALFORCE RAPC WORLDWIDE

(57) ABSTRACT

A needle-based device includes a barrel as a body thereof and a needle. A portion of the needle is received within the barrel and glued thereinto to cause the needle to protrude from the barrel. The needle-based device also includes a needle shield to protect an entire length of the needle protruding from the barrel based on completely encompassing the entire protruding length of the needle in a first state of disuse of the needle-based device. The barrel includes wings on lateral sides of an outer wall thereof. The wings extend perpendicular to a length of the barrel to couple the needle shield to the barrel in the first state of disuse of the needle-based device.

20 Claims, 19 Drawing Sheets

Related U.S. Application Data a continuation-in-part of application No. 17/234,793, filed on Apr. 19, 2021, now Pat. No. 11,224,699, said application No. 17/494,904 is a continuation of application No. 16/831,824, filed on Mar. 27, 2020, now Pat. No. 11,173,254, said application No. 17/234,793 is a continuation-in-part of application No. 16/831,824, filed on Mar. 27, 2020, now Pat. No. 11,173,254.

(51) Int. Cl.
*A61M 5/315* (2006.01)
*A61M 5/20* (2006.01)

(52) U.S. Cl.
CPC ...... *A61M 5/31571* (2013.01); *A61M 5/3234* (2013.01); *A61M 5/3243* (2013.01); *A61M 5/3257* (2013.01); *A61M 5/326* (2013.01); *A61M 5/3271* (2013.01); *A61M 2005/2073* (2013.01)

(58) Field of Classification Search
CPC ............ A61M 5/31571; A61M 5/3148; A61M 5/3134; A61M 5/3129; A61M 2005/3258; A61M 2005/3242; A61M 2005/3247; A61M 2005/3206; A61M 2005/2073
See application file for complete search history.

(56) References Cited

U.S. PATENT DOCUMENTS

| | | |
|---|---|---|
| 4,430,080 A | 2/1984 | Pasquini et al. |
| 4,631,057 A | 12/1986 | Mitchell |
| 4,636,201 A | 1/1987 | Ambrose et al. |
| 4,654,034 A | 3/1987 | Masters et al. |
| 4,664,654 A | 5/1987 | Strauss |
| 4,693,708 A | 9/1987 | Wanderer et al. |
| 4,735,617 A | 4/1988 | Nelson et al. |
| 4,752,290 A | 6/1988 | Schramm |
| 4,810,248 A | 3/1989 | Masters et al. |
| 4,826,488 A | 5/1989 | Nelson et al. |
| 4,863,435 A | 9/1989 | Sturman et al. |
| 4,887,998 A | 12/1989 | Martin et al. |
| 4,894,055 A | 1/1990 | Sudnak |
| 4,897,083 A | 1/1990 | Martell |
| 4,900,311 A * | 2/1990 | Stern ............... A61M 5/3271 604/263 |
| 4,911,693 A | 3/1990 | Paris |
| 4,915,701 A * | 4/1990 | Halkyard ............ A61M 5/3271 604/232 |
| 4,927,019 A | 5/1990 | Haber |
| 4,927,416 A | 5/1990 | Tomkiel |
| 4,932,940 A | 6/1990 | Walker et al. |
| 4,950,242 A | 8/1990 | Alvarez |
| 4,950,250 A | 8/1990 | Haber et al. |
| 4,952,207 A | 8/1990 | Lemieux |
| 4,964,866 A | 10/1990 | Szwarc |
| 4,966,592 A | 10/1990 | Burns et al. |
| 4,998,920 A | 3/1991 | Johnson |
| 4,998,922 A | 3/1991 | Kuracina et al. |
| 5,002,536 A | 3/1991 | Thompson et al. |
| 5,041,099 A | 8/1991 | Gelabert |
| 5,057,087 A | 10/1991 | Harmon |
| 5,085,647 A | 2/1992 | Henderson et al. |
| 5,104,385 A | 4/1992 | Huband |
| 5,104,386 A | 4/1992 | Alzain |
| 5,112,311 A | 5/1992 | Utterberg et al. |
| 5,135,504 A | 8/1992 | McLees |
| 5,152,750 A | 10/1992 | Haining |
| 5,154,699 A | 10/1992 | Ryan |
| 5,156,599 A | 10/1992 | Ranford et al. |
| 5,163,917 A | 11/1992 | Huefner et al. |
| 5,163,918 A | 11/1992 | Righi et al. |
| 5,181,524 A | 1/1993 | Wanderer et al. |
| 5,188,613 A | 2/1993 | Shaw |
| 5,193,552 A | 3/1993 | Columbus et al. |
| 5,207,646 A | 5/1993 | Brunel |
| 5,215,534 A | 6/1993 | De Harde et al. |
| 5,222,945 A | 6/1993 | Basnight |
| 5,246,427 A | 9/1993 | Sturman et al. |
| 5,254,099 A | 10/1993 | Kuracina et al. |
| 5,256,153 A | 10/1993 | Hake |
| 5,259,841 A | 11/1993 | Hohendorf et al. |
| 5,266,072 A | 11/1993 | Utterberg et al. |
| 5,267,961 A | 12/1993 | Shaw |
| 5,269,761 A | 12/1993 | Stehrenberger et al. |
| 5,300,040 A | 4/1994 | Martin |
| 5,304,149 A | 4/1994 | Morigi |
| 5,312,347 A | 5/1994 | Osborne et al. |
| 5,342,323 A | 8/1994 | Haining |
| 5,366,447 A | 11/1994 | Gurley |
| 5,368,577 A | 11/1994 | Teoh et al. |
| 5,385,557 A | 1/1995 | Thompson |
| 5,401,246 A | 3/1995 | Mazur et al. |
| 5,403,288 A | 4/1995 | Stanners |
| 5,411,487 A | 5/1995 | Castagna |
| 5,498,243 A | 3/1996 | Vallelunga et al. |
| 5,498,244 A | 3/1996 | Eck |
| 5,562,625 A | 10/1996 | Stefancin, Jr. |
| 5,582,594 A | 12/1996 | Chen |
| 5,591,138 A | 1/1997 | Vaillancourt |
| 5,647,849 A | 7/1997 | Kalin |
| 5,651,774 A | 7/1997 | Taranto et al. |
| 5,669,889 A | 9/1997 | Gyure et al. |
| 5,674,203 A | 10/1997 | Lewandowski |
| 5,688,241 A | 11/1997 | Asbaghi |
| 5,879,337 A | 3/1999 | Kuracina et al. |
| 5,997,513 A | 12/1999 | Smith et al. |
| 6,004,296 A | 12/1999 | Jansen et al. |
| 6,156,012 A | 12/2000 | Nathan |
| 6,162,197 A | 12/2000 | Mohammad |
| 6,224,569 B1 | 5/2001 | Brimhall |
| 6,394,983 B1 | 5/2002 | Mayoral et al. |
| 6,413,236 B1 | 7/2002 | Van Dyke |
| 6,436,075 B1 | 8/2002 | Liao |
| 6,537,257 B1 | 3/2003 | Wien |
| 6,558,360 B1 | 5/2003 | Olovson |
| 6,692,470 B2 | 2/2004 | Sanpietro |
| 6,752,788 B2 | 6/2004 | Tuen |
| 6,776,775 B1 | 8/2004 | Mohammad |
| 6,817,989 B2 | 11/2004 | Svendsen et al. |
| 6,918,889 B1 | 7/2005 | Brunel |
| 6,926,697 B2 | 8/2005 | Malenchek |
| 7,282,042 B2 | 10/2007 | Wang |
| 7,300,420 B2 | 11/2007 | Doyle |
| 7,314,464 B2 | 1/2008 | Giambattista et al. |
| 7,329,238 B2 | 2/2008 | Halseth et al. |
| 7,381,199 B2 | 6/2008 | Kuan |
| 7,455,661 B2 | 11/2008 | Barrelle et al. |
| 7,462,168 B2 | 12/2008 | Stonehouse et al. |
| 7,497,847 B2 | 3/2009 | Crawford et al. |
| 7,566,324 B2 | 7/2009 | Hommann et al. |
| 7,727,190 B2 | 6/2010 | Miller |
| 7,799,002 B2 | 9/2010 | Dillard, III |
| 7,837,659 B2 | 11/2010 | Bush, Jr. et al. |
| 7,854,723 B2 | 12/2010 | Hwang et al. |
| 7,922,698 B2 | 4/2011 | Riesenberger et al. |
| 8,016,797 B2 | 9/2011 | Gratwohl et al. |
| 8,062,265 B2 | 11/2011 | Millerd |
| 8,172,810 B2 | 5/2012 | Liversidge |
| 8,226,630 B2 | 7/2012 | Ackerman |
| 8,323,251 B2 | 12/2012 | West et al. |
| 8,337,467 B2 | 12/2012 | Rimlinger et al. |
| 8,337,468 B1 | 12/2012 | Reis et al. |
| 8,398,597 B2 | 3/2013 | Brimhall |
| 8,545,454 B2 | 10/2013 | Kuracina et al. |
| 8,591,474 B2 | 11/2013 | Gratwohl et al. |
| 8,617,119 B2 | 12/2013 | Liversidge |
| 8,747,355 B2 | 6/2014 | Rubinstein et al. |
| 8,858,508 B2 | 10/2014 | Lavi et al. |
| 8,864,718 B2 | 10/2014 | Karlsen et al. |
| 8,936,575 B2 | 1/2015 | Moulton |
| 9,022,979 B2 | 5/2015 | Woehr |
| 9,248,244 B2 | 2/2016 | Roberts et al. |

(56) References Cited

U.S. PATENT DOCUMENTS

| | | | |
|---|---|---|---|
| 9,333,306 | B2 | 5/2016 | Cross et al. |
| 9,352,099 | B2 | 5/2016 | Roberts et al. |
| 9,421,336 | B2 | 8/2016 | Ekman et al. |
| 9,555,221 | B2 | 1/2017 | Koehler et al. |
| 9,579,467 | B2 | 2/2017 | Karlsson |
| 9,586,011 | B2 | 3/2017 | Roberts et al. |
| 9,649,452 | B2 | 5/2017 | Srinivasan et al. |
| 9,750,894 | B2 | 9/2017 | Quinn et al. |
| 9,757,527 | B2 | 9/2017 | Bokelman et al. |
| 9,931,476 | B2 | 4/2018 | Zhang et al. |
| 10,010,684 | B2 | 7/2018 | McDown et al. |
| 10,092,322 | B2 | 10/2018 | Albert et al. |
| 10,166,334 | B2 | 1/2019 | Wyrick |
| 10,220,157 | B2 | 3/2019 | Nguyen |
| 10,335,555 | B2 | 7/2019 | Klippenstein |
| 10,357,621 | B2 | 7/2019 | Gupta et al. |
| 10,426,901 | B2 | 10/2019 | Cho |
| 10,478,568 | B2 | 11/2019 | Evans et al. |
| 10,485,920 | B2 | 11/2019 | Bendix et al. |
| 10,518,041 | B2 | 12/2019 | Brereton et al. |
| 10,518,042 | B2 | 12/2019 | Keim et al. |
| 10,668,217 | B2 | 6/2020 | Fabien et al. |
| 10,814,069 | B2 | 10/2020 | Takemoto |
| 10,821,236 | B2 | 11/2020 | Limaye |
| 10,926,036 | B2 | 2/2021 | Shluzas et al. |
| 11,020,535 | B2 | 6/2021 | Shi et al. |
| 11,065,395 | B2 | 7/2021 | Schoonmaker |
| 11,116,911 | B2 | 9/2021 | Wu |
| 11,318,256 | B2 | 5/2022 | Alexandersson |
| 11,376,373 | B2 | 7/2022 | Perot et al. |
| 11,426,529 | B2 | 8/2022 | Hommann et al. |
| 2002/0138042 | A1* | 9/2002 | Llorach ............. A61M 5/343 422/26 |
| 2003/0055383 | A1 | 3/2003 | Bush et al. |
| 2003/0181860 | A1 | 9/2003 | Swenson |
| 2003/0187401 | A1 | 10/2003 | Doyle |
| 2004/0030294 | A1 | 2/2004 | Mahurkar |
| 2005/0113750 | A1 | 5/2005 | Targell |
| 2005/0171486 | A1 | 8/2005 | Hochman |
| 2005/0209568 | A1 | 9/2005 | Shanley |
| 2005/0240160 | A1 | 10/2005 | Lin |
| 2005/0277892 | A1 | 12/2005 | Chen |
| 2006/0100589 | A1 | 5/2006 | Lin |
| 2006/0173409 | A1 | 8/2006 | Yang |
| 2006/0282044 | A1 | 12/2006 | Mohammed |
| 2007/0073224 | A1 | 3/2007 | Dries |
| 2007/0078409 | A1 | 4/2007 | Saltz |
| 2008/0177238 | A1 | 7/2008 | Follman et al. |
| 2009/0157010 | A1 | 6/2009 | Martin |
| 2011/0137261 | A1 | 6/2011 | Garber et al. |
| 2012/0022463 | A1 | 1/2012 | Wu |
| 2013/0030365 | A1 | 1/2013 | Liversidge |
| 2013/0035643 | A1 | 2/2013 | Kawamura |
| 2013/0079715 | A1 | 3/2013 | Wu |
| 2013/0261559 | A1 | 10/2013 | Werbickas |
| 2013/0261564 | A1 | 10/2013 | Wong |
| 2014/0039406 | A1 | 2/2014 | Verespej et al. |
| 2014/0088513 | A1 | 3/2014 | Darichuk et al. |
| 2015/0038922 | A1 | 2/2015 | Slemmen et al. |
| 2015/0133870 | A1 | 5/2015 | Ashworth et al. |
| 2015/0272492 | A1 | 10/2015 | Schraga |
| 2017/0182260 | A1 | 6/2017 | Schraga |
| 2018/0161520 | A1 | 6/2018 | Smith et al. |
| 2018/0200487 | A1 | 7/2018 | Sokolski et al. |
| 2018/0243514 | A1 | 8/2018 | Kim et al. |
| 2020/0398002 | A1 | 12/2020 | Mesa et al. |
| 2021/0299361 | A1 | 9/2021 | Moleda |
| 2021/0299364 | A1 | 9/2021 | Moleda |
| 2022/0072238 | A1 | 3/2022 | Julian et al. |

FOREIGN PATENT DOCUMENTS

| | | |
|---|---|---|
| EP | 3360592 A1 | 8/2018 |
| EP | 3017838 B1 | 5/2019 |
| EP | 2883563 B1 | 3/2021 |
| KR | 200191613 Y1 | 8/2000 |
| KR | 20190128609 A | 11/2019 |
| KR | 102185590 B1 | 12/2020 |
| KR | 20230058935 A | 5/2023 |
| TW | 506843 B | 10/2002 |
| WO | 1990014112 A1 | 11/1990 |
| WO | 9220390 A1 | 11/1992 |
| WO | 1994004205 A1 | 3/1994 |
| WO | 1997027891 A1 | 8/1997 |
| WO | 1998031407 A1 | 7/1998 |
| WO | 2001045776 A1 | 6/2001 |
| WO | 2003015855 A1 | 2/2003 |
| WO | 2003066141 A1 | 8/2003 |
| WO | 2003082385 A1 | 10/2003 |
| WO | 2004060445 A2 | 7/2004 |
| WO | 2007077463 A1 | 7/2007 |
| WO | 2008127195 A1 | 10/2008 |
| WO | 2011107954 A2 | 9/2011 |
| WO | 2011162913 A1 | 12/2011 |
| WO | 2012000834 A1 | 1/2012 |
| WO | 2012000835 A1 | 1/2012 |
| WO | 2012045350 A1 | 4/2012 |
| WO | 2012093073 A1 | 7/2012 |
| WO | 2013064475 A1 | 5/2013 |
| WO | 2017069316 A1 | 4/2017 |
| WO | 2017179813 A1 | 10/2017 |
| WO | 2018079962 A1 | 5/2018 |
| WO | 2018111797 A2 | 6/2018 |
| WO | 2019010689 A1 | 1/2019 |
| WO | 2021191670 A1 | 9/2021 |
| WO | 2022051470 A1 | 3/2022 |
| WO | 2022052575 A1 | 3/2022 |
| WO | 2023072578 A1 | 5/2023 |

OTHER PUBLICATIONS

"ONE_CARE Insulin Safety Syringes" by Medivena, Found Online on [May 31, 2021] https://static1.squarespace.com/static/5c2e33d43917eeb9b98da746/t/5e85017fc8068858c09e1e44/1585774982210/ONE-CARE%E2%84%A2+Insulin+Safety+Syringes+_+website.pdf.

"Single Use Safety Syringe With Passive Needlestick Injury & Reuse Prevention" By Alfa Corpuscles Pvt. Ltd., Found Online On [May 31, 2021] https://birac.nic.in/product-detail.php?product=56.

"Ritract safety syringe" by BerryDesign, Published online in 2005 https://www.berrydesign.com.au/portfolios/medical/ritract-safety-syringe.php.

"An introduction to needlestick protection and safety syringes" by Springboard, Published Online on [Jun. 13, 2018] https://www.springboard.pro/safety-syringes/.

"The hypodermic syringe performance based on the ISO 7886-1:2017" by Krisdiyanto, Found Online on [Dec. 9, 2022] https://www.ncbi.nim.nih.gov/pmc/articles/PMC9750608/pdf/medi-101-e31812.pdf.

"Spotlight On Safety" by UCR Environmental Health & Safety, Found Online on [Oct. 20, 2023] https://ehs.ucr.edu/sites/default/files/2021-01/Bio_6_syringe.pdf.

"Instructions for Use UDENYCA® (yoo-den-i-kah) (pegfilgrastim-cbqv Injection" by Coherus BioSciences, Inc., Found Online on [Oct. 20, 2023] https://udenyca.com/pdf/udenyca-instructions-for-use_pfs.pdf.

"Instructions for Use Xolair® (ZOHL-air)" by Genentech, Inc., Found Online on [Oct. 20, 2023] https://www.gene.com/download/pdf/xolair_ifu.pdf.

"Safety-engineered needles and syringes" by BD, Found Online on [Oct. 20, 2023] https://www.krackeler.com/pdf/BD_Product_Catalog.pdf.

\* cited by examiner

US 12,005,244 B2

NEEDLE-BASED DEVICE BASED ON DIRECT WING-BASED COUPLING OF A NEEDLE SHIELD TO A BARREL THEREOF AND SAFETY MECHANISM IMPLEMENTED THEREIN

CLAIM OF PRIORITY

This Application is a Continuation-in-Part Application of, and claims priority to, co-pending U.S. patent application Ser. No. 17/494,904 titled "NEEDLE-BASED DEVICE WITH A SAFETY MECHANISM IMPLEMENTED THEREIN" filed on Oct. 6, 2021, which is a U.S. Continuation Application of U.S. patent application Ser. No. 16/831,824 titled "NEEDLE-BASED DEVICE WITH A SAFETY MECHANISM IMPLEMENTED THEREIN" filed on Mar. 27, 2020 and issued on Nov. 16, 2021 as U.S. Pat. No. 11,173,254, and U.S. patent application Ser. No. 17/234,793 also titled "NEEDLE-BASED DEVICE WITH A SAFETY MECHANISM IMPLEMENTED THEREIN" filed on Apr. 19, 2021 and issued as U.S. Pat. No. 11,224,699 on Jan. 18, 2022. U.S. patent application Ser. No. 17/234,793 is a Continuation-in-Part Application of and claims priority to U.S. patent application Ser. No. 16/831,824. The contents of each of the aforementioned applications are incorporated in entirety thereof in this Application by reference.

FIELD OF TECHNOLOGY

This disclosure relates generally to needle-based devices and, more particularly, to a needle-based device based on direct wing-based coupling of a needle shield to a barrel thereof and a safety mechanism implemented therein.

BACKGROUND

A needle-based device may be a syringe, a hypodermic needle, a pen injector and/or a fluid collection device. A needle of the needle-based device may be attached to a needle mount, which, in turn, may be attached to a barrel of the needle-based device. The attachment of the needle to the needle mount may not be stable. Further, the needle mount, although modular in terms of assembly of the needle-based device, may add to a number of components required to assemble the needle-based device

SUMMARY

Disclosed are methods, a device and/or a system of a needle-based device based on direct wing-based coupling of a needle shield to a barrel thereof and a safety mechanism implemented therein.

In one aspect, a needle-based device includes a barrel as a body thereof and a needle. A portion of the needle is received within the barrel and glued thereinto to cause the needle to protrude from the barrel. The needle-based device also includes a needle shield to protect an entire length of the needle protruding from the barrel based on completely encompassing the entire protruding length of the needle in a first state of disuse of the needle-based device. The barrel includes wings on lateral sides of an outer wall thereof. The wings extend perpendicular to a length of the barrel to couple the needle shield to the barrel in the first state of disuse of the needle-based device.

In another aspect, a needle-based device includes a barrel as a body of the needle-based device and a needle. The barrel includes a needle port proximate an end thereof integrally formed with the barrel, Thee needle port is within an inner cross-sectional width of the barrel and concentric with an outer wall of the barrel. The needle port extends from the end of the barrel thereinto within the inner cross-sectional width of the barrel such that the needle port is entirely encompassed within the inner cross-sectional width of the barrel. An outer boundary of the needle port along a length of the barrel is at most flush with an outer cross-sectional boundary of the barrel at the end of the barrel.

A portion of the needle is received within an inner cross-sectional width of the needle port and glued thereinto to cause the needle to protrude from the barrel. The needle-based device also includes a needle shield to protect an entire length of the needle protruding from the barrel based on completely encompassing the entire protruding length of the needle in a first state of disuse of the needle-based device. The barrel includes wings on lateral sides of the outer wall thereof. The wings extend perpendicular to the length of the barrel to couple the needle shield to the barrel in the first state of disuse of the needle-based device.

In yet another aspect, a needle-based device includes a barrel as a body of the needle-based device, a needle and a needle shield. A portion of the needle is received within the barrel and glued thereinto to cause the needle to protrude from the barrel. The needle shield protects an entire length of the needle protruding from the barrel based on completely encompassing the entire protruding length of the needle in a first state of disuse of the needle-based device. The needle-based device also includes a lock button with a first end. The first end is either integrally formed with the needle shield or external to the needle shield and then coupled to the needle shield. A length of the lock button is completely external to the needle shield.

The needle shield is locked with the lock button in the first state of disuse of the needle-based device based on the lock button including a hook at a second end thereof that passes through a groove formed on the needle shield and locks onto a top of the barrel from which the needle protrudes such that, in the state of the locking of the needle shield, the length of the lock button completely external to the needle shield is parallel to a length of the needle shield and the entire protruding length of the needle, and the hook is perpendicular to the length of the needle shield, the length of the lock button and the entire protruding length of the needle.

The barrel includes wings on lateral sides of an outer wall thereof. The wings extend perpendicular to a length of the barrel to couple the needle shield to the barrel in the first state of disuse of the needle-based device.

Other features will be apparent from the accompanying drawings and from the detailed description that follows.

BRIEF DESCRIPTION OF THE DRAWINGS

The embodiments of this invention are illustrated by way of example and not limitation in the figures of the accompanying drawings, in which like references indicate similar elements and in which.

Other features of the present embodiments will be apparent from the accompanying drawings and from the detailed description that follows.

DETAILED DESCRIPTION

Example embodiments, as described below, may be used to provide methods, a system and/or a device of a needle-based device based on direct wing-based coupling of a needle shield to a barrel thereof and a safety mechanism implemented therein. Although the present embodiments have been described with reference to specific example embodiments, it will be evident that various modifications and changes may be made to these embodiments without departing from the broader spirit and scope of the various embodiments.

Figure 1:
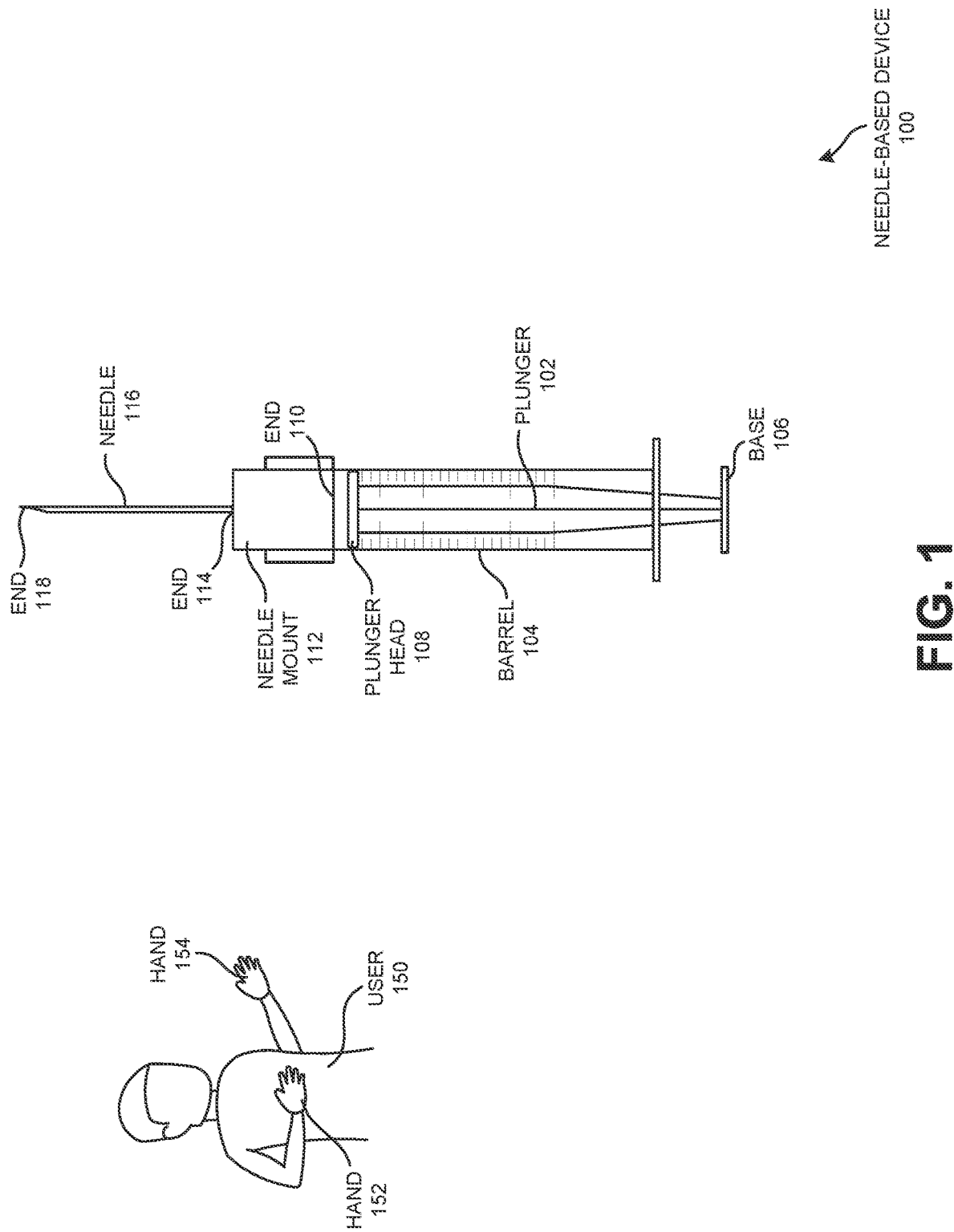
FIG. 1 is a schematic view of a needle-based device, according to one or more embodiments.

FIG. 1 shows a needle-based device 100, according to one or more embodiments. In one or more embodiments, needle-based device 100 may be a syringe, a hypodermic needle, a pen injector, a fluid (e.g., blood) collection device and/or a fluid injector/extractor. It should be noted that needle-based device 100 may not only be limited in use to medical applications but may also be used in biological applications and/or chemical applications. For example, needle-based device 100 may be used to extract a requisite quantity of a solvent/fluid from a vial/bottle. All reasonable applications are within the scope of the exemplary embodiments discussed herein.

In one or more embodiments, needle-based device 100 may include a plunger 102 configured to be moved in and out of a barrel 104 thereof. In one example implementation, barrel 104 may be cylindrical and plunger 102 may be appropriately designed (e.g., also cylindrical) to enable slidable movement thereof within barrel 104 and in and out of barrel 104. In another example implementation, barrel 104 may be shaped like a square prism or a rectangular prism and plunger 102 may be appropriately shaped to enable the aforementioned slidable movement. All possible shapes and configurations of barrel 104 and plunger 102 that enable the slidable movement of plunger 102 within barrel 104 and in and out of barrel 104 are within the scope of the exemplary embodiments discussed herein.

In one or more embodiments, a base 106 of plunger 102 may enable a user 150 to press plunger 102 into barrel 104 using a thumb of a hand 152 thereof; base 106 may also enable user 150 to draw plunger 102 out of barrel 104 using the thumb and/or other fingers of hand 152. In one or more embodiments, user 150 may be able to use the other fingers (e.g., forefinger and middle finger) and, optionally, a palm of hand 152 to stabilize needle-based device 100 while utilizing the thumb to press plunger 102 into barrel 104; user 150 may hold needle-based device 100 through another hand (e.g., hand 154) and draw plunger 102 out of barrel 104 using the thumb and/or the other fingers of hand 152. The use of plunger 102 and barrel 104 are well known to one skilled in the art with respect to needle-based devices; detailed discussion thereof is, therefore, skipped for the sake of convenience, brevity and clarity.

It should be noted that, in all states of operation of needle-based device 100, at least some portion of plunger 102 (e.g., at least base 106) may be outside barrel 104. It should also be noted that at least some portion of plunger 102 may be inside barrel 104 in all states of operation of needle-based device 100. For example, an end of plunger 102 farthest away from an end thereof including base 106 may be a plunger head 108. In one or more embodiments, plunger head 108 may be inside barrel 104 in all states of operation of needle-based device 100. In one or more embodiments, as shown in FIG. 1, a cross-sectional diameter of plunger head 108 may be less than a cross-sectional diameter of barrel 104, and a cross-sectional diameter of base 106 may be more than the cross-sectional diameter of barrel 104. The aforementioned designs are crucial to enable plunger 102 to move within barrel 104 to perform functionalities associated with needle-based device 100. Without base 106, it may not be possible for a position of plunger head 108 within barrel 104 to be desirably controlled. Without plunger head 108, plunger 102 may fall out of barrel 104 in a vertical position of needle-based device 100 with base 106 at a bottom thereof. Also, a portion of barrel 104 between plunger head 108 and an end 110 of barrel 104 farthest away from base 106 may include a fluid drawn from a vial/bottle by needle-based device 100. Said portion may not be able to hold the fluid without plunger head 108.

FIG. 1 also shows a needle mount 112, according to one or more embodiments. In one or more embodiments, an end 114 of a needle 116 may be inserted into needle mount 112 (e.g., a needle hub) such that needle 116 protrudes from needle mount 112. In one or more embodiments, needle 116 may include a hollow (e.g., cylindrical) bore along a length thereof. In one or more embodiments, another end 118 of needle 116 may be beveled into a point. In one or more embodiments, end 118 of needle 116 may be configured to first touch a vial/bottle during extraction of a fluid therefrom or an arm of a patient during injection of the fluid therein. In one or more embodiments, needle mount 112, in turn, may be directly coupled to barrel 104 by way of end 110 thereof farthest from base 106. Thus, in an implementation where barrel 104 and plunger 102 together may form a syringe, needle mount 112 and, thereby, needle 116 may be attached to the syringe.

Figure 2:
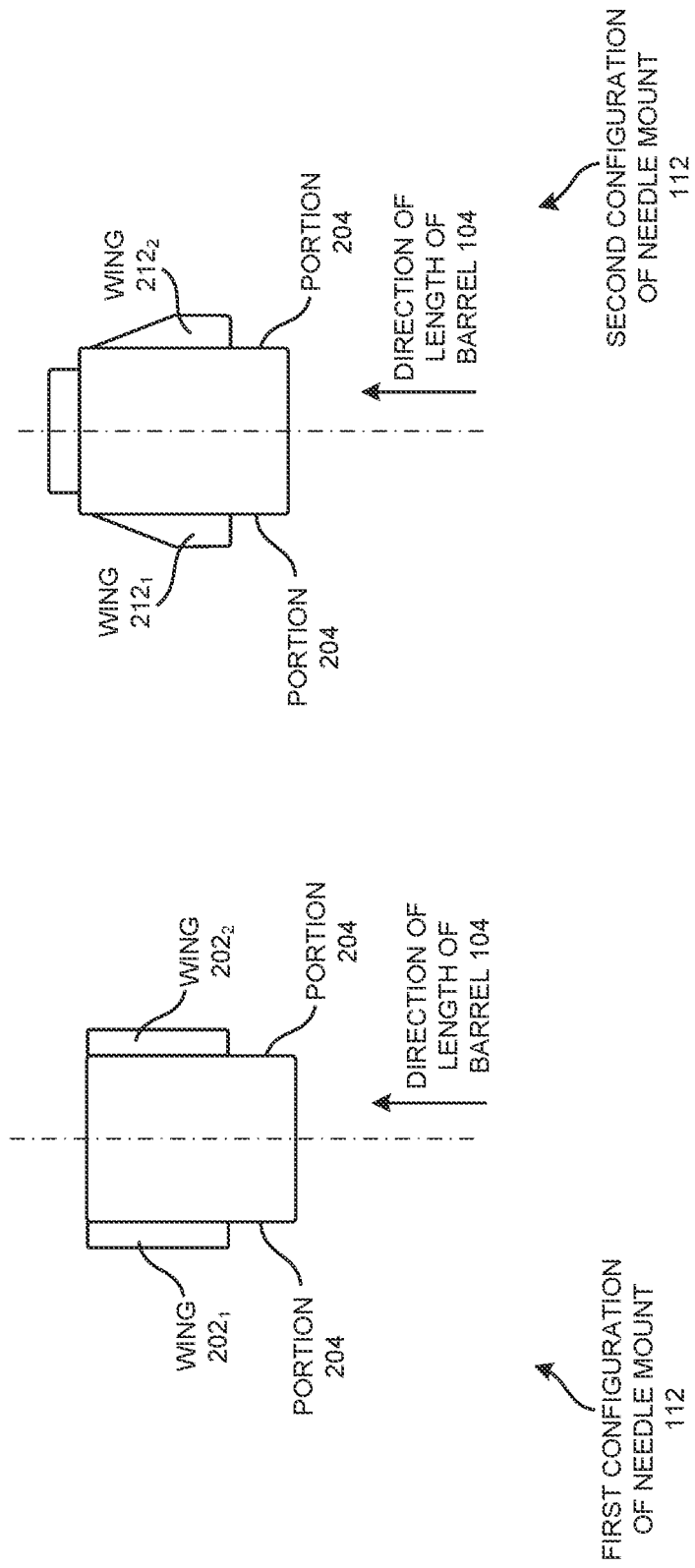
FIG. 2 is a schematic view of multiple configurations of a needle mount of the needle-based device of FIG. 1, according to one or more embodiments.

FIG. 2 shows multiple configurations of needle mount 112, according to one or more embodiments. In a first configuration, needle mount 112 may have a wing $202_{1,2}$ on each lateral side thereof in a direction approximately perpendicular (or perpendicular) to a length of barrel 104 when needle mount 112 is coupled to barrel 104. A portion 204 of needle mount 112 with no wings may be configured to be directly coupled (e.g., based on a screw mechanism) to barrel 104. In the first configuration, wings $202_{1-2}$ may be of uniform width. In a second configuration, again, needle mount 112 may have a wing $212_{1,2}$ on each lateral side thereof in the direction approximately perpendicular (or perpendicular) to the length of barrel 104 when needle mount 112 is coupled to barrel 104. Again, in the second configuration, a portion 214 of needle mount 112 with no wings may be configured to be directly coupled (e.g., based on a screw mechanism) to barrel 104. However, unlike the first configuration, wings $212_{1-2}$ may be only partially of uniform width, only to then taper off to a reduced width (or no width).

Figure 3:
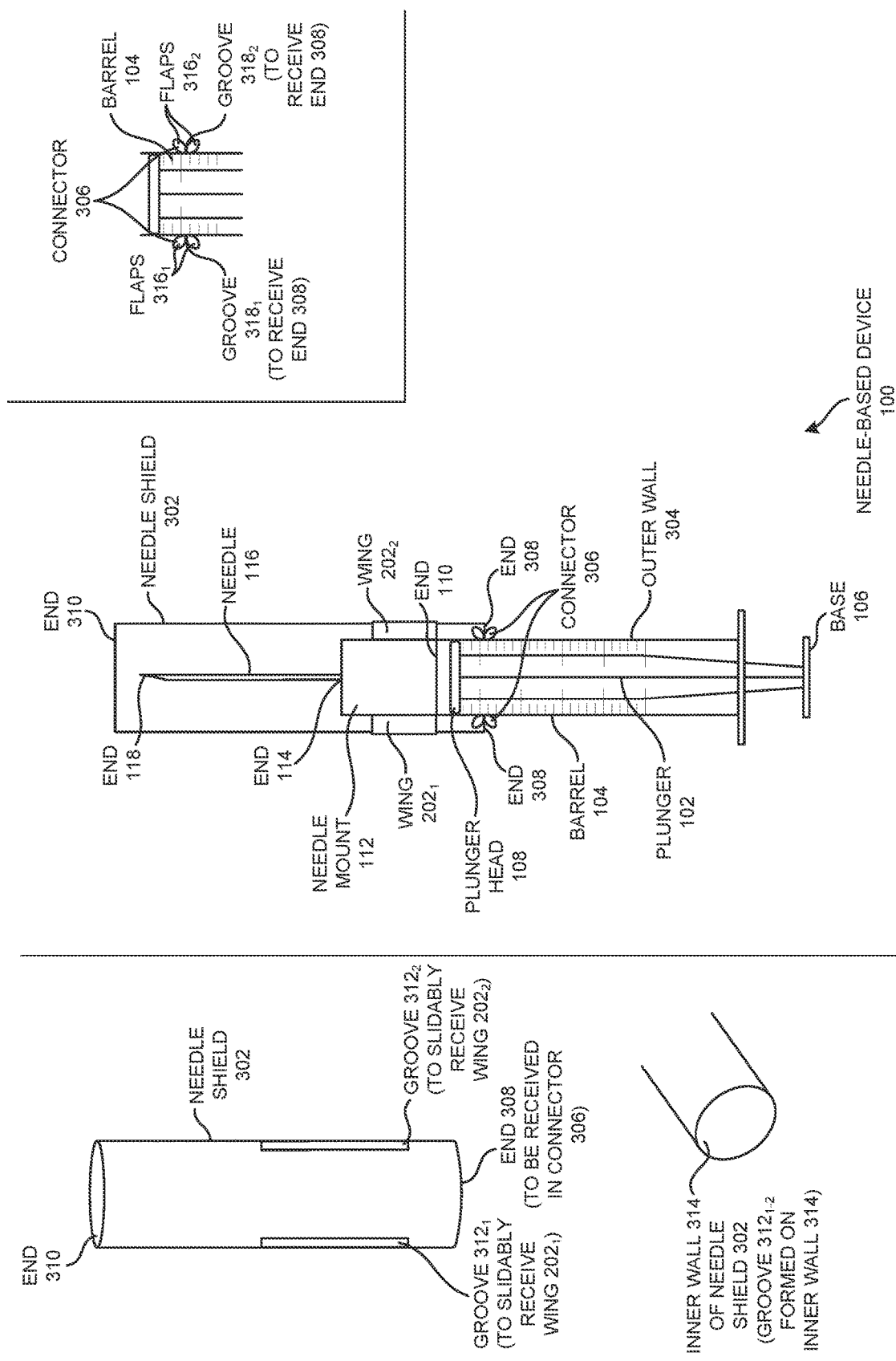
FIG. 3 is a schematic view of coupling of a needle shield to the needle-based device of FIG. 1 to encompass a needle thereof, according to one or more embodiments.

FIG. 3 shows coupling of a needle shield 302 to needle-based device 100 to encompass needle 116 thereof, according to one or more embodiments. Here, in one or more embodiments, needle shield 302 may be cylindrical or shaped like a rectangular prism/square prism based on the design of needle mount 112 and/or barrel 104. Additionally, in one or more embodiments, needle shield 302 may be hollow to enable encompassing the protruding needle 116 therewithin. In one or more embodiments, an outer wall 304 of barrel 104 proximate end 110 may have a connector 306 thereon to enable an end 308 of needle shield 302 to clasp onto connector 306 while needle shield 302 completely encompasses the protruding needle 116 therewithin. In one or more embodiments, an inner cross-sectional diameter of needle shield 302 may be more than an outer cross-sectional diameter of needle mount 112 and an outer cross-sectional diameter of barrel 104 to enable the sliding of needle shield 302 over needle mount 112 and barrel 104.

In one or more embodiments, needle shield 302 may first receive the protruding needle 116 on needle mount 112 through end 308 thereof. In one or more embodiments, needle shield 302 may then be slid over needle mount 112 until end 308 clasps onto connector 306 on outer wall 304 of barrel 104. In the state of needle shield 302 completely encompassing the protruding needle 116, the other end (e.g., end 310) of needle shield 302 may completely enclose end 118 of needle 116. FIG. 3 shows needle shield 302 to be transparent (e.g., needle shield 302 may be made of plastic, glass etc.). However, it should be noted that needle shield 302 may be translucent or opaque in certain embodiments. Here, the outer wall of needle shield 302 may include cuts (not shown) that reveal needle 116 while needle 116 is still protected by needle shield 302. All reasonable variations are within the scope of the exemplary embodiments discussed herein.

In one or more embodiments, the sliding of needle shield 302 over needle mount 112 may be facilitated by wings $202_{1-2}$ on needle mount 112. For the aforementioned purpose, optionally, grooves $312_{1-2}$ may be provided on an inner wall 314 of needle shield 302. In one or more embodiments, wings $202_{1-2}$ of needle mount 112 may be received within grooves $312_{1-2}$ during relative sliding of wings $202_{1-2}$ with respect to grooves $312_{1-2}$. While FIG. 3 shows grooves $312_{1-2}$ as cutting across inner wall 314 of needle shield 302 into an entire thickness thereof, it should be noted that grooves $312_{1-2}$ may not cut across inner wall 314 of needle shield 302 completely in one or more alternative embodiments. In one or more embodiments, needle shield 302 may slide until reception thereof within connector 306. In one or more embodiments, connector 306 may be constituted by flexible pairs of flaps $316_{1-2}$, each forming a groove $318_{1-2}$ to receive end 308 of needle shield 302 therewithin.

Thus, in one or more embodiments, user 150 may cover needle 116 with needle shield 302 for temporary protection (e.g., for transportation to a site of a patient). In one or more embodiments, needle 116 may be covered using needle shield 302 also after use thereof. In one or more embodiments, the covering of needle 116 with needle shield 302 may not only protect needle 116 but also prevent undesirable accidents arising out of unwanted contact therewith. In one or more embodiments, in order to enable injection of a fluid (e.g., a medication) into a body of a patient, needle 116 may be uncovered based on pushing needle shield 302 further downward. In one or more embodiments, as connector 306 may be flexible, user 150 may be able to apply enough downward pressure to enable end 308 of needle shield 302 to pop out of grooves $318_{1-2}$ of connector 306 and slide further downward along barrel 104. In one or more embodiments, during the course of needle shield 302 sliding further downward along barrel 104, needle 116 pops out of end 310 of needle shield 302 such that needle 116 is uncovered.

In one or more embodiments, needle shield 302 may indirectly move further downward along barrel 104 when user 150, after drawing plunger 102 outward from barrel 104, places needle shield 302 against a cap of a vial or a bottle and pushes barrel 104 inward toward the vial or the bottle. In one or more embodiments, this may automatically cause end 308 of needle shield 302 to pop out of grooves $318_{1-2}$ of connector 306 and slide further downward along barrel 104, thereby uncovering needle 116. In one or more embodiments, user 150 may hold needle shield 302 to maintain a position thereof in which needle 116 is exposed to inject a fluid (e.g., medication) into a body of a patient or extract blood therefrom. In one or more embodiments, once the task is done, a force may be applied in an opposite direction on needle shield 302 by user 150 to restore a state of complete encompassment of needle 116 by needle shield 302.

Thus, in one or more embodiments, needle-based device 100 may be provided with needle shield 302 configured to protect needle 116 in a state of disuse thereof (e.g., storage, transportation, post-injection of a fluid, post-collection of a fluid) and to be retractable to reveal needle 116 for use (e.g., injection of a fluid, collection of a fluid) thereof. It should be noted that while FIGS. 2 and 3 show wings ($202_{1-2}$, $212_{1-2}$) on lateral sides of needle mount 112, it is possible that wings may be present on lateral sides of barrel 104 instead in one or more alternative embodiments. Here, in one or more embodiments, needle mount 112 may be smaller in size and plainer. Also, it should be noted that needle shield 302 need not be coupled to barrel 104 merely by way of connector 306. In certain embodiments, needle shield 302 may merely be mounted on an element analogous to needle mount 112. In this case, said element may encompass needle mount 112 and needle shield 302 may be indirectly coupled to barrel 104 by way of being coupled to said element. In certain cases, needle mount 112 may also be interpreted as a mount (e.g., based on the element encompassing needle mount 112) for needle shield 302.

Figure 4:
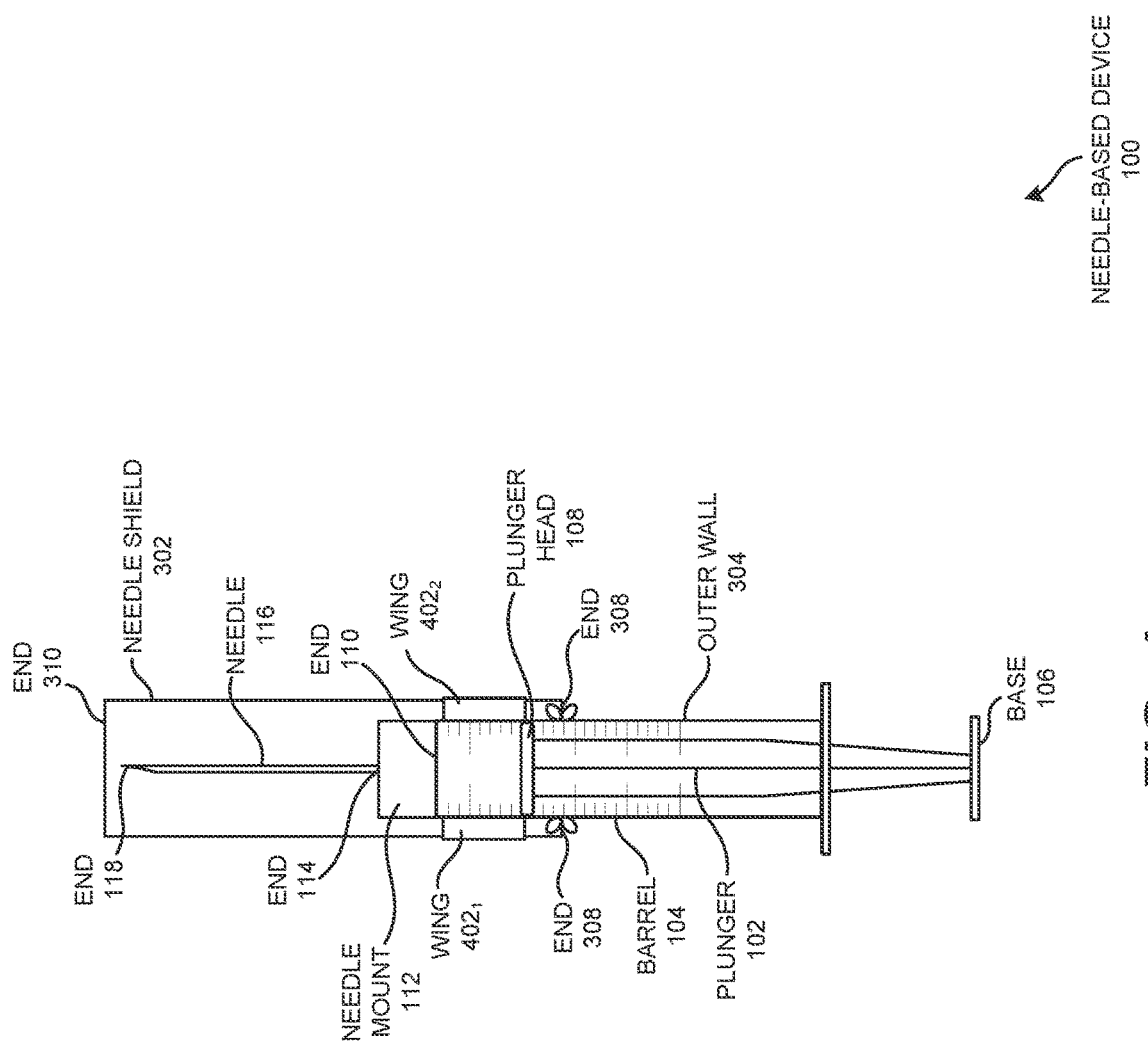
FIG. 4 is a schematic view of the needle-based device of FIG. 1 with wings on lateral sides of an outer wall of a barrel thereof, according to one or more embodiments.

FIG. 4 shows needle-based device 100 with wings $402_{1-2}$ on lateral sides of barrel 104 on outer wall 304 thereof proximate end 110, according to one or more embodiments. Here, in one or more embodiments, needle shield 302 may slide over wings $402_{1-2}$ to lock onto connector 306 on outer wall 304 to shield needle 116. In one or more embodiments, needle shield 302 may pushed further downward along barrel 104, thereby uncovering/revealing needle 116, based on pressure applied to needle shield 302 such that end 308 pops out of connector 306. Again, in one or more embodiments, needle shield 302 may be pulled back to a position in which needle shield 302 completely encompasses the protruding needle 116.

It is to be noted that while FIG. 4 shows wings $402_{1-2}$ in a configuration similar to the first configuration thereof in needle mount 112 of FIG. 2, wings $402_{1-2}$ may also be in a configuration similar to the second configuration thereof in needle mount 112 of FIG. 2. Further, all reasonable variations that allow for relative movement between needle shield 302 and needle mount 112/barrel 104 are within the scope of the exemplary embodiments discussed herein. In FIG. 4, needle mount 112 may be smaller than the embodiments of FIGS. 2-3 because of the absence of wings thereon.

Referring back to FIG. 3, it should be noted that configuration of wings $202_{1-2}$ therein may, again, not be limited. It may be possible for wings $212_{1-2}$ to be on lateral sides of needle mount 112 instead of wings $202_{1-2}$. Further, as discussed above, grooves $312_{1-2}$ may not completely cut across inner wall 314 of needle shield 302. In this embodiment, wings $212_{1-2}$ may be received within grooves $312_{1-2}$ and may slide relatively thereto. Here, the tapering on wings $212_{1-2}$ may enable needle shield 302 to be locked onto needle mount 112/barrel 104, without a requirement of connector 306. Again, needle shield 302 may be pushed downward to reveal/uncover needle 116, as discussed above. Needle shield 302 may then be manually restored to an original position thereof in which needle shield 302 completely encompasses the protruding needle 116.

Figure 5:
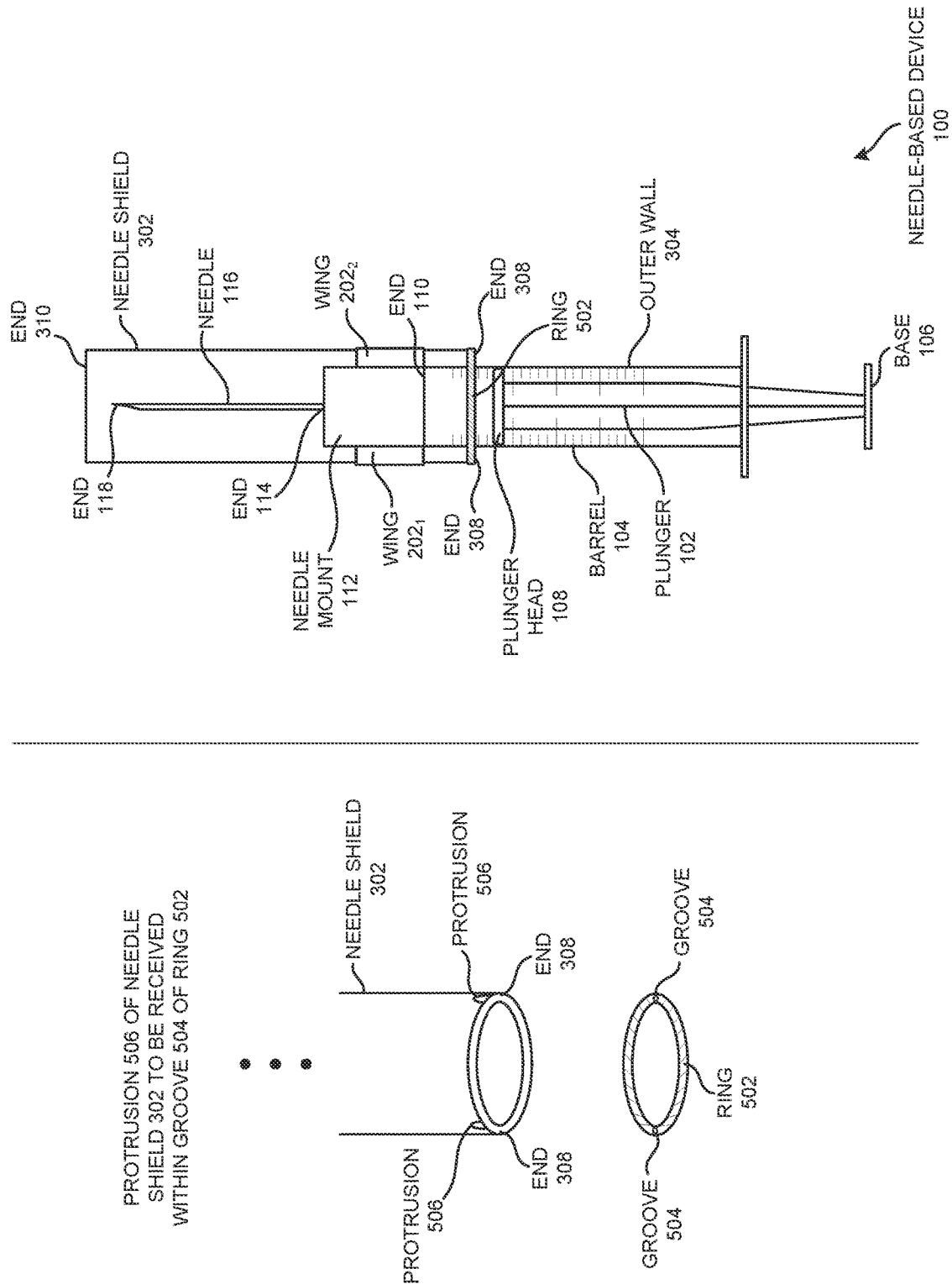
FIG. 5 is a schematic view of the needle-based device of FIG. 1 with a ring on the outer wall of the barrel thereof, according to one or more embodiments.

FIG. 5 shows needle-based device 100 with a ring 502 on outer wall 304 of barrel 104 proximate end 110, according to one or more embodiments. Here, needle mount 112 may be in the same configurations as in FIGS. 2-3; alternatively, needle mount 112 may be smaller and without any wings thereon. In one implementation, ring 502 (e.g., of uniform thickness) may protrude from outer wall 304 of barrel 104; in addition, an underside of ring 502 may have a groove 504 complementary to a protrusion 506 on end 308 of needle shield 302. Again, needle shield 302 may first receive needle 116 on needle mount 112 through end 308 thereof. Needle shield 302 may be moved downward toward barrel 104 such that, after a point, protrusion 506 of needle shield 302 locks onto groove 504 of ring 502. In this state, needle shield 302 may completely encompass the protruding needle 116 therewithin.

In one or more embodiments, ring 502 may be made of a flexible material. Also, in one or more implementations, while ring 502 may change shape due to flexibility thereof, ring 502 may not change a position thereof along barrel 104. In one or more embodiments, an appropriate downward pressure (e.g., by user 150) may enable protrusion 506 to pop out of groove 504 and cause needle shield 302 to go further downward along barrel 104. In one or more embodiments, this may uncover/reveal needle 116 for use on a patient (e.g., to extract blood, to inject a fluid, to prick a finger) or on a vial/bottle (e.g., to extract a fluid). In one or more embodiments, following use of needle 116, an upward pressure may be applied to enable protrusion 506 to once again lock into groove 504 to enable needle shield 302 completely encompass needle 116 again.

The ring (e.g., ring 502) embodiment of FIG. 5 is merely an example embodiment. Other embodiments involving rings that facilitate covering of needle 116 and uncovering thereof are within the scope of the exemplary embodiments discussed herein. In one or more embodiments, wings ($202_{1-2}$, $212_{1-2}$) on needle mount 112 may further aid the locking/unlocking/relocking of needle shield 302 at/from appropriate positions. All reasonable variations are within the scope of the exemplary embodiments discus sed herein.

Figure 6:
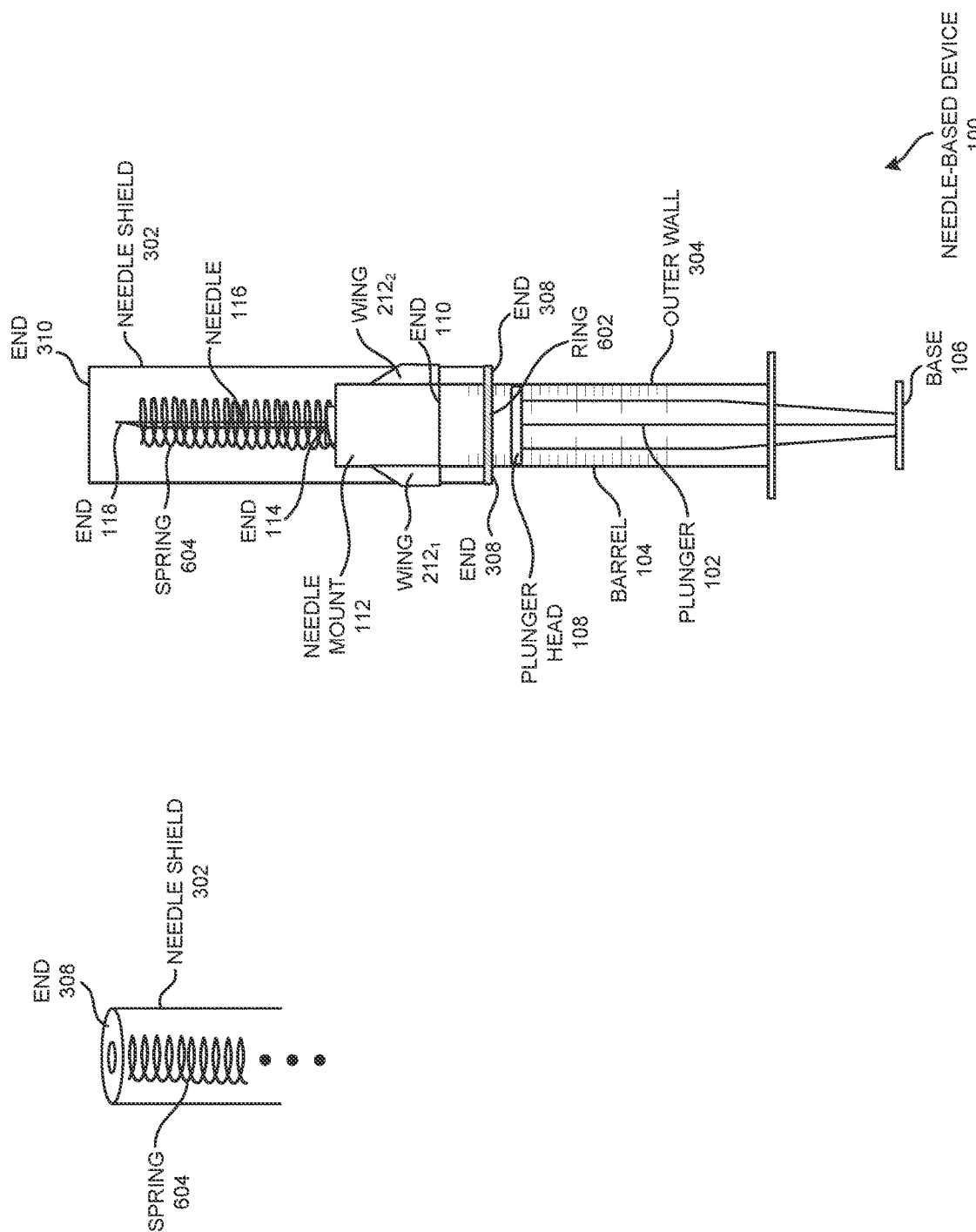
FIG. 6 is a schematic view of the needle-based device of FIG. 1 in a spring-based configuration of a needle shield thereof, according to one or more embodiments.

FIG. 6 shows needle-based device 100 in a spring-based configuration of needle shield 302, according to one or more embodiments. Here, in one or more embodiments, needle mount 112 with wings $212_{1-2}$ may be directly inserted into barrel 104 via end 110 farthest from base 106. In one example implementation, barrel 104 may have grooves (not shown) on an inside wall thereof proximate end 110 onto which needle mount 112 may be screwed. Other forms of coupling needle mount 112 to barrel 104 are within the scope of the exemplary embodiments discussed herein. In one or more embodiments, barrel 104 may have a ring 602 (e.g., analogous to ring 502, but may be structurally different; ring 602 may be made of flexible material) formed on outer wall 304 thereof proximate end 110. In some embodiments, ring 602 may be integrally formed with barrel 104, while in some other embodiments, ring 602 may be an element separate from barrel 104.

In one or more embodiments, a spring 604 may be placed over needle mount 112 such that spring 604 encompasses the protruding needle 116 along an entire length thereof. In one or more embodiments, now when spring 604 encompassing needle 116 is received within needle shield 302 through end 308 thereof and needle shield 302 is moved downward toward barrel 104, end 308 of needle shield 302 may press against ring 602. In one or more embodiments, further application of pressure (e.g., through hand 152 of user 150) may compress ring 602 and push ring 602 inside end 308 to be received within needle shield 302. In one or more embodiments, in this state, needle shield 302 may completely encompass the entire lengths of both protruding needle 116 and spring 604.

In one or more embodiments, when no further external pressure is applied, needle shield 302 may comfortably shield the protruding needle 116 and spring 602. In one or more embodiments, although ring 602 may not lock needle shield 302 in a position, needle shield 302 may be prevented from falling outward when needle-based device 100 is flipped over because a cross-sectional inner diameter of ring 602 may be more than a cross-sectional inner diameter of end 308. In one or more embodiments, needle shield 302 may be hollow. In one or more embodiments, further, a cross-sectional inner diameter of end 310 of needle shield 302 farthest away from end 308 may be smaller than a cross-sectional diameter of spring 604. Thus, in one or more embodiments, needle shield 302 may be prevented from falling downward by spring 604 when needle-based device 100 is held in an upright position.

In one or more embodiments, if spring 604 were not present, needle shield 302 may slip and fall downward; alternatively or additionally, needle shield 302 may be prevented from falling downward based on an element mounted on needle mount 112, as discussed above. However, in one or more embodiments, upon further application of pressure in a downward direction toward barrel 104 by user 150 or by pressing end 310 of needle shield 302 against a surface (e.g., an arm of a patient, a cap of a vial/bottle) that exerts a normal reaction in the downward direction, needle shield 302 moves in the downward direction along barrel 104, thereby compressing spring 604 also in the same direction to uncover/reveal needle 116. In one or more embodiments, the uncovered/revealed needle 116 may then be utilized appropriately (e.g., for injecting a fluid into a patient, for pricking a finger/body part of the patient, for pricking a cap of a vial/bottle). Following use of needle 116, the force along the direction of compression of spring 604 may be relaxed (e.g., by taking needle-based device 100 out of the surface, user 150 stopping the application of pressure in the downward direction) to enable spring 604 revert to an uncompressed version thereof; in the uncompressed state of spring 604, needle shield 302 may once again completely encompass the protruding needle 116 and spring 604.

In other words, immediately following relaxation of the application of the force along the direction of compression of spring 604, needle-based device 100 may be automatically transitioned back to the state of disuse thereof (e.g., a state where needle shield 302 completely encompasses needle 116 and spring 604) following use thereof in accordance with another force (e.g., a restoring force) provided by decompression of spring 604 that is automatically applied in a direction diametrically opposite to the direction of compression of spring 604.

In the scenario of injecting a fluid into the body of a patient, needle-based device 100 may first be placed against a cap of a vial/bottle from which the fluid is to be extracted. When end 310 is pressed against the cap, the normal reaction from the cap pushes needle shield 302 downward, thereby compressing spring 604. The downward movement of needle shield 302 and the compression of spring 604 exposes needle 116 that pricks the cap. Plunger 102 may also be pushed in by way of user 150 pressing base 106 in an upward direction toward needle mount 112 such that plunger head 108 contacts needle mount 112. Now, pulling plunger 102 back may create a gap between needle mount 112 and plunger head 108. Said gap may constitute a low pressure region, thereby enabling the fluid to fill the gap by way of gushing in through the hollow needle 116.

Now, the desired quantity of the fluid may be filled in the gap. The gap may be controlled based on graduated marks (e.g., shown as graduated marks 606) on barrel 104. Once the desired quantity of fluid is available in the gap, user 150 may take needle-based device 100 out of the vial/bottle, thereby decompressing spring 604 to restore spring 604 to the original shape thereof. User 150 may then place end 310 of needle shield 302 against the arm of a patient, which, again, compresses spring 604 as discussed above, and exposes needle 116. The exposed needle 116 may prick a skin of the patient; the pressing of base 106 may compress a volume of the gap, thereby creating a high pressure region therein. The fluid may be squeezed through the hollow needle 116 into the body of the patient.

Once the fluid is injected into the body of the patient, needle-based device 100 may be extracted out of the arm of the patient. This decompresses spring 604 and restores needle shield 302 to the position in which needle shield 302 completely encompasses the exposed needle 116 and spring 604. Needle-based device 100 may also be employed to prick a finger tip of the patient to extract blood or to extract another fluid from a bottle/vial; additionally, needle-based device 100 may be used to extract venom from a body portion of a mammal. The details with respect to the figures discussed above make the aforementioned uses obvious. All reasonable variations are within the scope of the exemplary embodiments discussed herein.

With respect to FIG. 6, it is obvious that needle shield 302 may be retracted to reveal needle 116 and released to close needle 116 at will. Also, wings $212_{1-2}$ on needle mount 112 may aid the secure coupling between needle shield 302 and barrel 104. It is possible to envision the embodiment of FIG. 6 without wings $212_{1-2}$. To summarize, the embodiment of FIG. 6 may be employed in two distinct modes of operation with respect to the use of needle-based device 100 where needle shield 302 is retracted to compress spring 604 and to reveal needle 116. In one or more embodiments, the first distinct mode of operation of use of needle-based device 100 may be the extraction of a fluid from a vial/bottle or a body (e.g., arm) of a mammal (e.g., a human), and the second distinct mode of operation of use of needle-based device 100 may be the injection of said fluid into the body of the mammal or a body of another mammal. No current solutions exist where an analogous needle is shielded and exposed for use during both the extraction of a fluid and the injection thereof. Yet another mode of operation of the embodiment of FIG. 6 may be related the state of disuse of needle-based device 100 where needle 116 is completely shielded/encompassed by spring 604 and needle shield 302.

Figure 7:
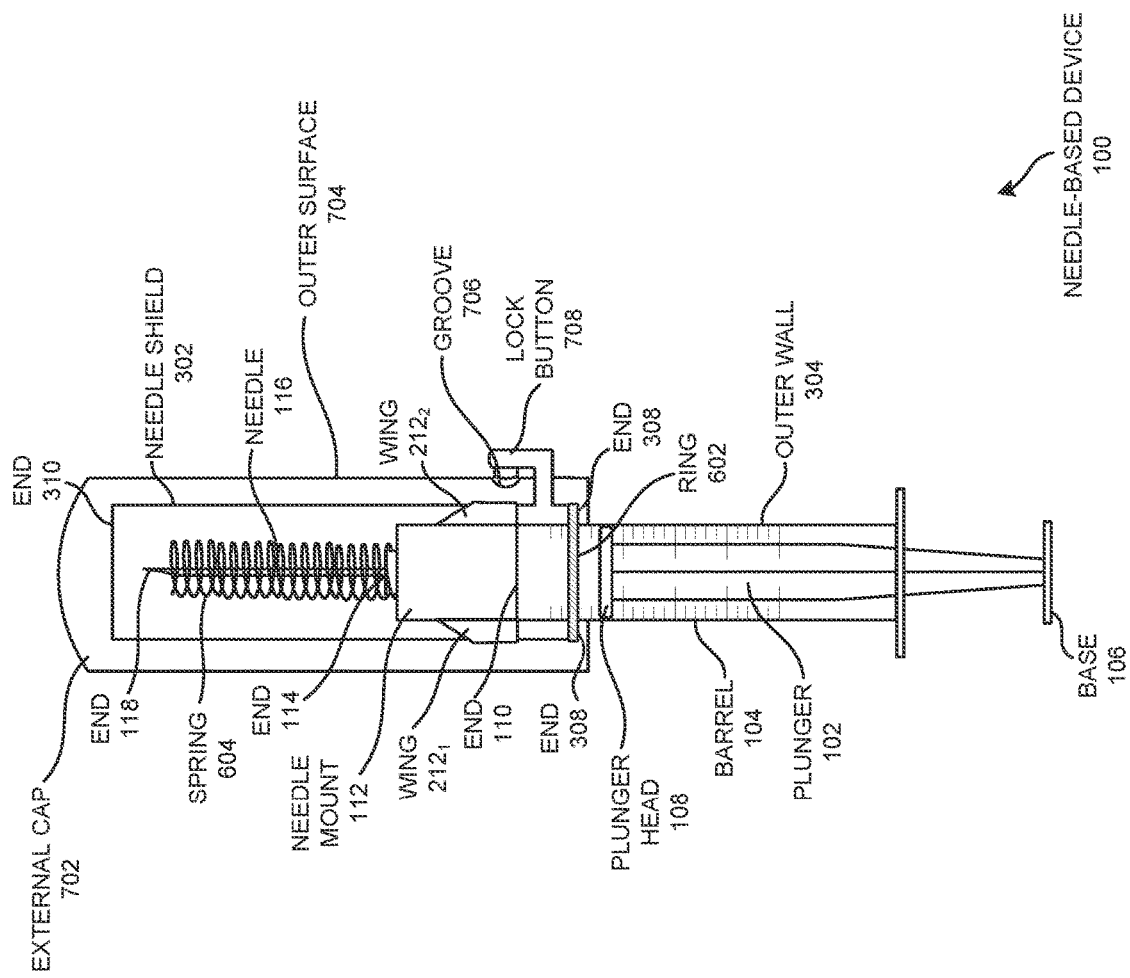
FIG. 7 is a schematic view of an external cap configured to at least partially cover the needle shield of the needle-based device of FIGS. 1 and 3, according to one or more embodiments.

FIG. 7 shows an external cap 702 configured to at least partially cover needle shield 302, according to one or more embodiments. In one or more embodiments, external cap 702 may be made of a transparent (e.g., plastic, glass), a translucent (e.g., rubber) or an opaque material to cover the slits and cuts on needle shield 302. In one or more embodiments, an outer surface 704 of external cap 702 may have a groove 706 therein. Correspondingly, in one or more embodiments, needle shield 302 may have a lock button 708 on an outer surface thereof. In one or more embodiments, lock button 708 of needle shield 302 may be configured to be received into groove 706 on external cap 702 to lock needle-based device 100 (e.g., in a state of disuse thereof).

In one or more embodiments, the use of external locking may prevent reuse of needle-based device 100, or at least needle 116 therein. Although FIG. 7 shows needle shield 302 as covering needle 116 and spring 604, concepts associated with the external locking may also be applicable across the embodiments of FIGS. 1-5. In one or more embodiments, the external locking may prevent movement of needle shield 302, which, in turn, prevents reuse of needle-based device 100. Alternatively, needle shield 302 itself may include both lock button 708 and groove 706. Here, locking may be done merely using elements of needle shield 302. In another alternative implementation, lock button 708 may be external to needle shield 302. For example, lock button 708 may be on external cap 702 and groove 706 may be on needle shield 302. Here, lock button 708 of external cap 702 may be received within groove 706 of needle shield 302.

In yet another alternative implementation, external cap 702 may cover lock button 708 of needle shield 302 to prevent premature/accidental locking during transportation or handling of needle-based device 100. In one example implementation, external cap 702 may be designed like a pen cap. Other configurations of external cap 702 are within the scope of the exemplary embodiments herein.

Thus, exemplary embodiments discussed above provide for safety mechanisms with respect to needle-based device 100. The manual shielding available in typical syringes may require capping a needle after use thereof. The capping and uncapping may cause needle injuries to a user. Additionally, in a spring-based typical implementation of a syringe that allows for a needle to be retracted therewithin, some space may be reserved in a barrel for the spring. This may result in loss of space for medication. The automatic retraction of needle shield 302 in the exemplary embodiments discussed herein may also allow for one-handed operation of needle-based device 100. All reasonable variations are within the scope of the exemplary embodiments discussed herein.

It should be noted that exemplary embodiments discussed above have been placed in the context of a syringe and needle 116, with barrel 104 and plunger 102. However, concepts associated with the exemplary embodiments discussed herein are applicable across embodiments where needle mount 112 is coupled to a body (alternative to barrel 104) of needle-based device 100 and needle 116 protrudes from needle mount 112. In one or more embodiments, needle shield 302 may encompass the protruding needle 116 in a state of operation; needle shield 302 may be retracted to reveal/uncover needle 116. In one or more embodiments, needle shield 302 may also be protected through external cap 702, as discussed above. All reasonable variations in and combinations of the exemplary embodiments discussed with respect to FIGS. 1-7 are within the scope of the exemplary embodiments discussed herein.

Figure 8:
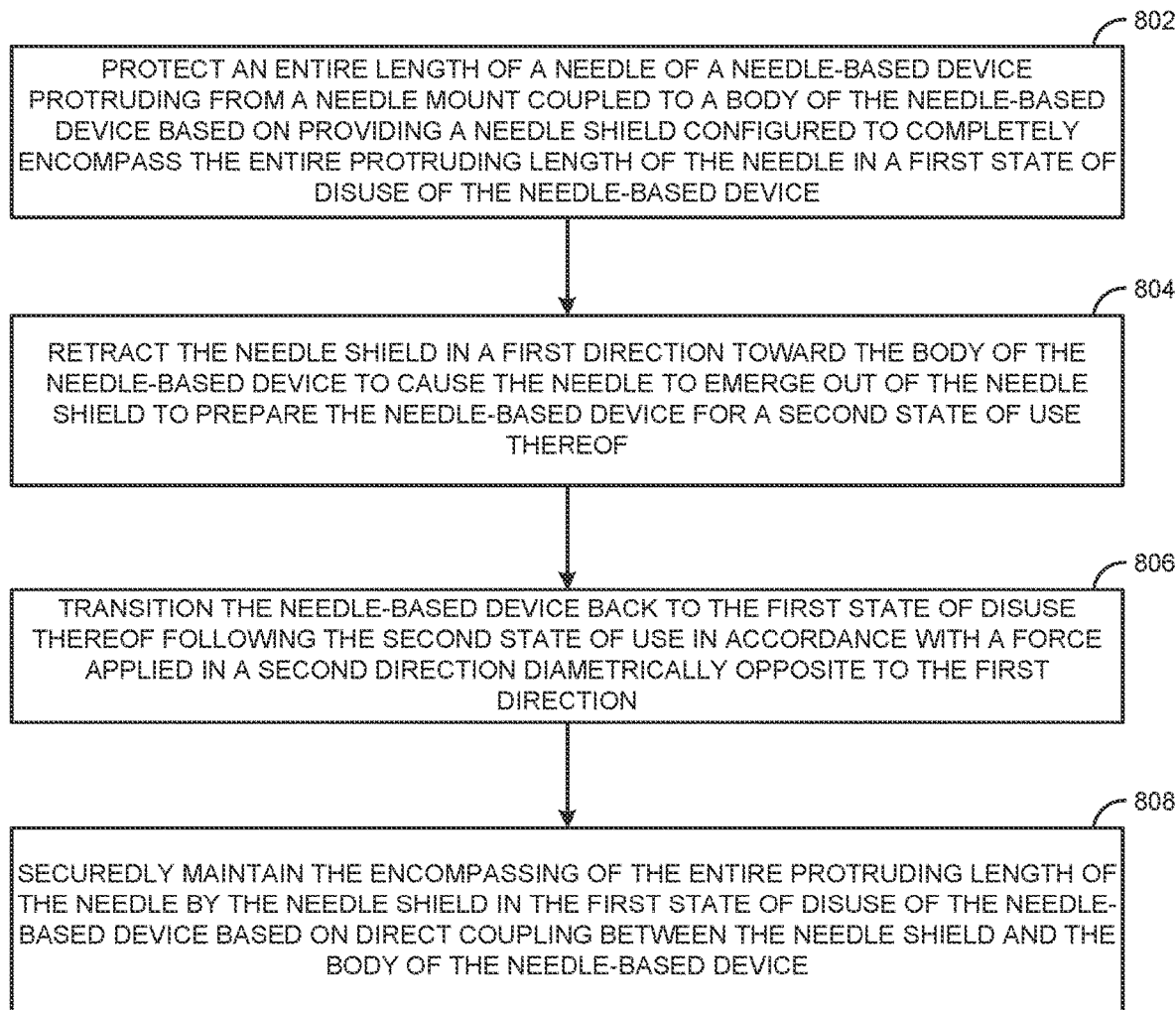
FIG. 8 is a process flow diagram detailing the operations involved in implementing a security mechanism in the needle-based device of FIG. 1, according to one or more embodiments.

FIG. 8 shows a process flow diagram detailing the operations involved in implementing a security mechanism in a needle-based device (e.g., needle-based device 100), according to one or more embodiments. In one or more embodiments, operation 802 may involve protecting an entire length of a needle (e.g., needle 116) of the needle-based device protruding from a needle mount (e.g., needle mount 112) coupled to a body (e.g., barrel 104) of the needle-based device based on providing a needle shield (e.g., needle shield 302) configured to completely encompass the entire protruding length of the needle in a first state of disuse of the needle-based device. In one or more embodiments, operation 804 may involve retracting the needle shield in a first direction toward the body of the needle-based device to cause the needle to emerge out of the needle shield to prepare the needle-based device for a second state of use thereof.

In one or more embodiments, operation 806 may involve transitioning the needle-based device back to the first state of disuse thereof following the second state of use in accordance with a force applied in a second direction diametrically opposite to the first direction. In one or more embodiments, operation 808 may then involve securely maintaining the encompassing of the entire protruding length of the needle by the needle shield in the first state of disuse of the needle-based device based on coupling between the needle shield and the body of the needle-based device.

Figure 9:
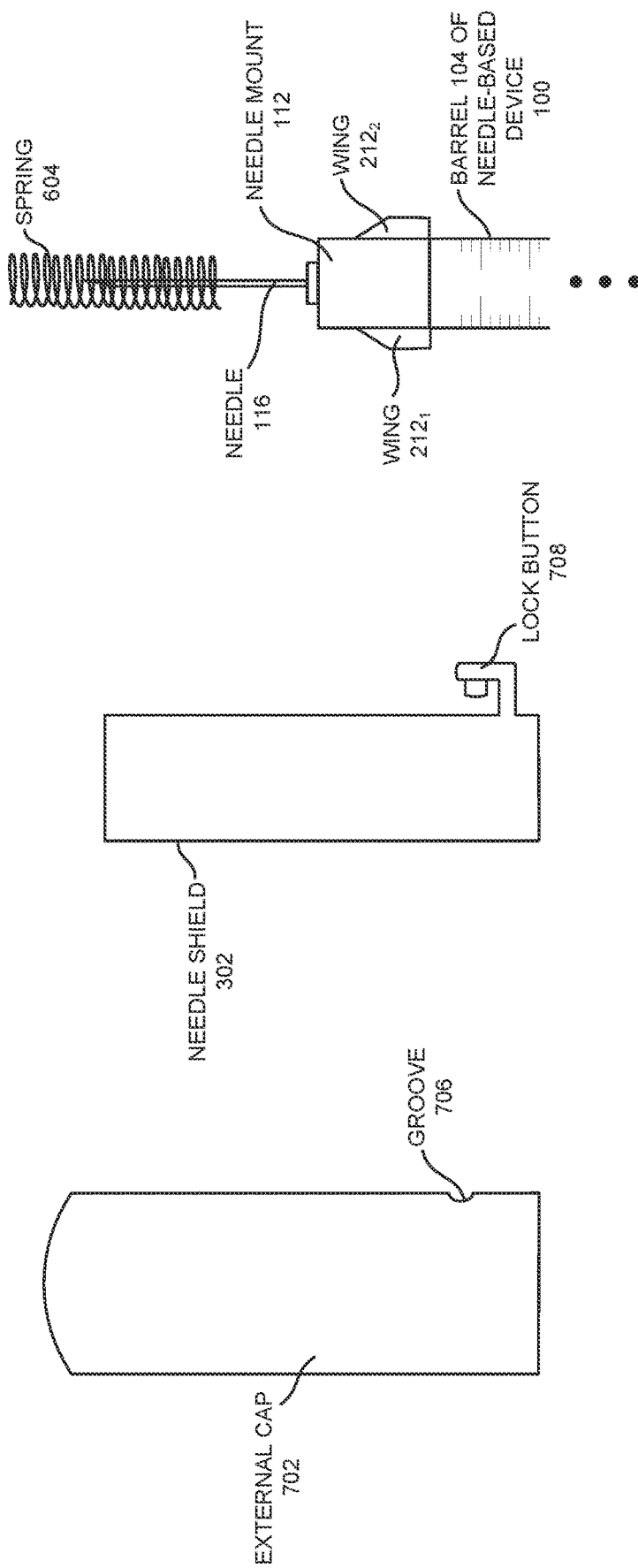
FIG. 9 is a schematic view of the spring-based embodiment of FIGS. 6-7 with external cap, needle mount and needle shield thereof as modular elements.

FIG. 9 shows the spring-based embodiment of FIGS. 6-7 with external cap 702, needle mount 112 and needle shield 302 as modular elements. In one or more embodiments, as clearly indicated by FIGS. 6 and 9 and as discussed above, needle shield 302 may be mounted onto barrel 104 (body of needle-based device 100) directly or, for example, through the user of a connector (such as ring 602) such that needle shield 302 encompasses both spring 604 and needle 116. As discussed with reference to FIG. 6, the relative cross-sectional areas/diameters of needle mount 112, needle shield 302 and ring 602 may automatically enable protection of needle 116 and prevent accidental sticks caused by needle 116 otherwise. It should be noted that there may be snaps (not shown) formed on barrel 104 (or body of needle-based device 100) to enable direct coupling of needle shield 302 thereonto.

Figure 10:
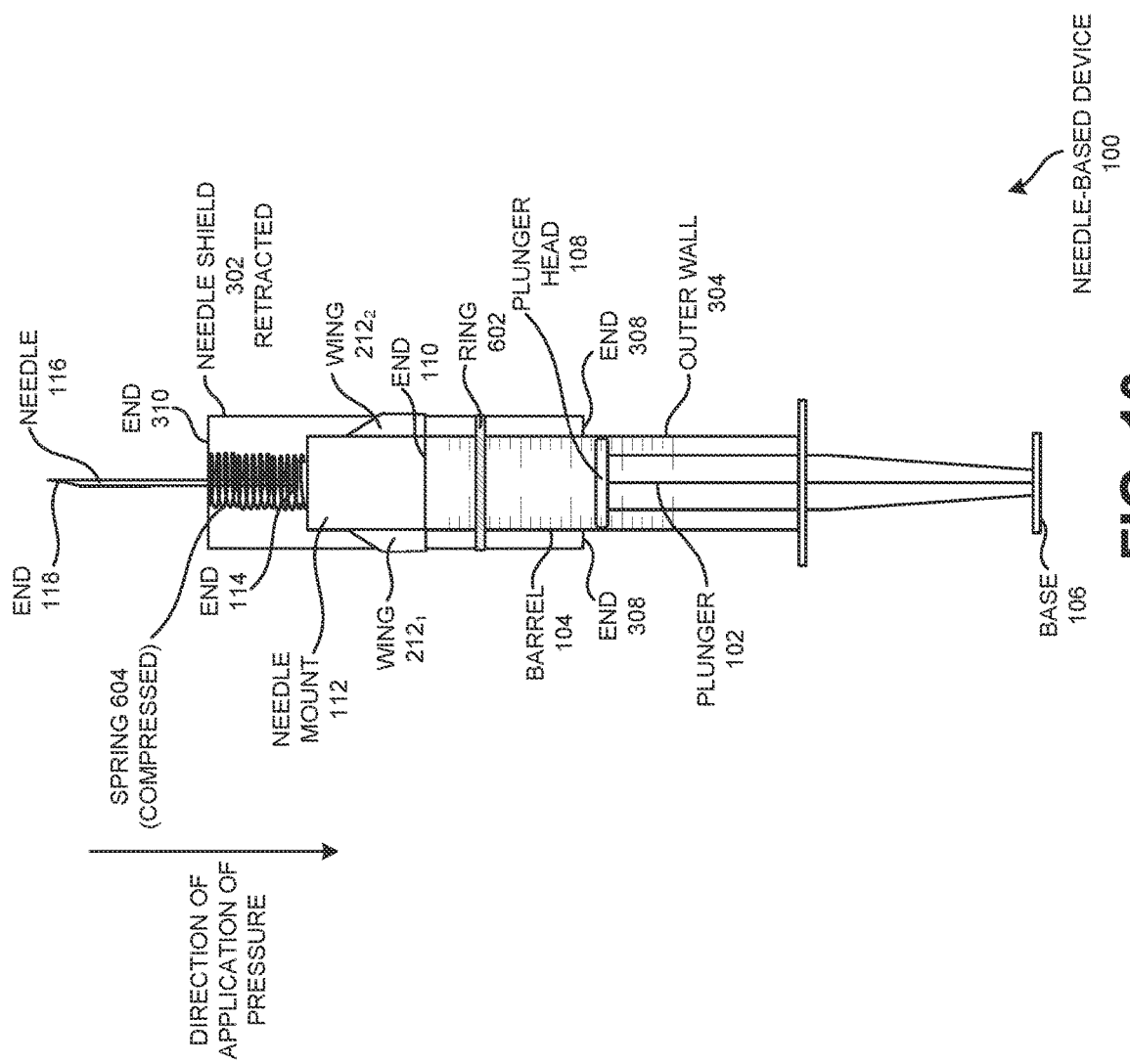
FIG. 10 is an illustrative view of retraction of the needle shield in the spring-based embodiment of FIG. 6.
Figure 11:
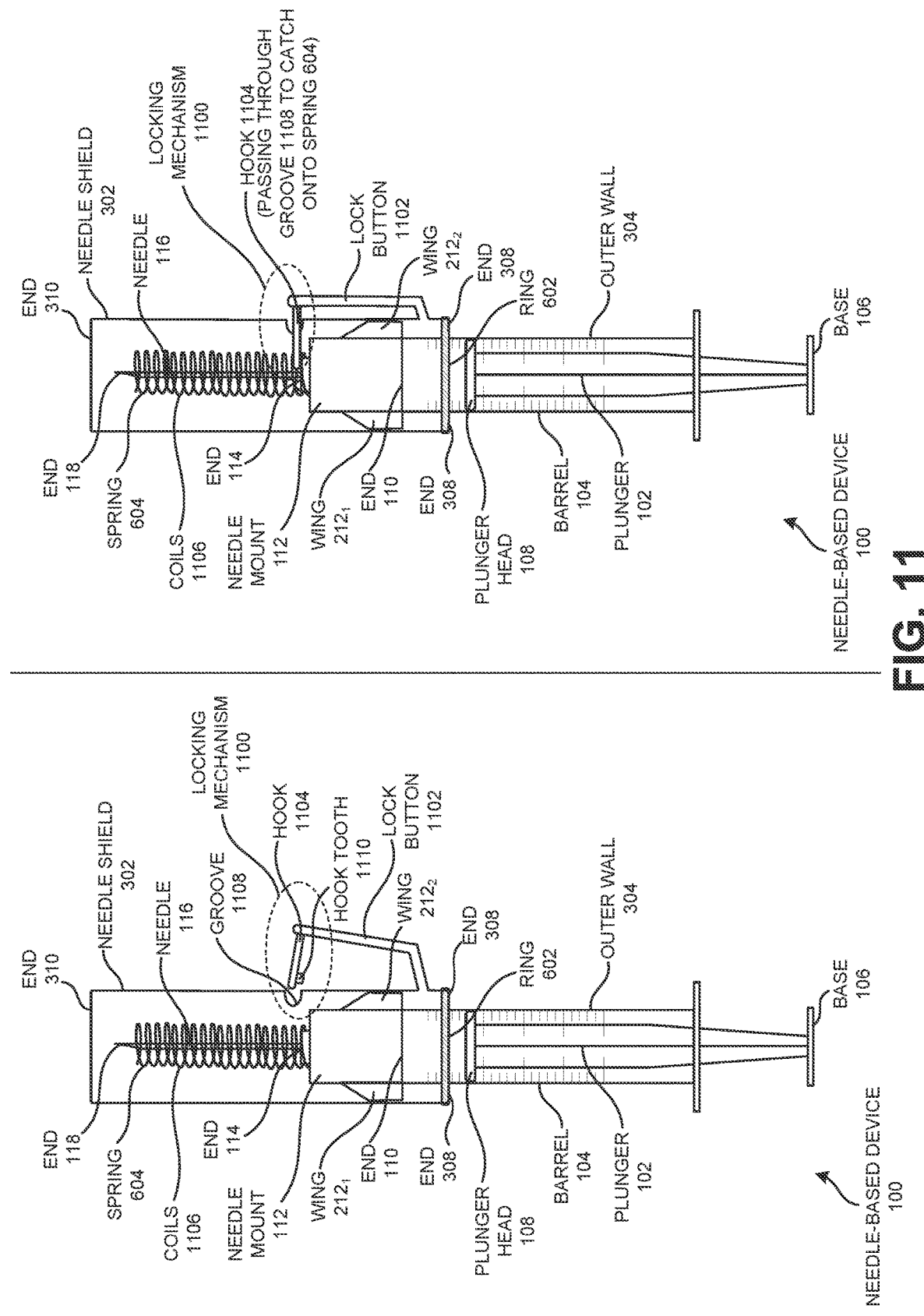
FIG. 11 is a schematic view of a locking mechanism of a needle-based device in accordance with the embodiments of FIGS. 6 and 7, but as a variant thereof.

FIG. 10 shows retraction of needle shield 302 in the spring-based embodiment of FIG. 6, according to one or more embodiments. As discussed above, once pressure is applied in a downward direction toward barrel 104 by user 150 or by pressing end 310 of needle shield 302 against a surface (e.g., an arm of a patient, a cap of a vial/bottle), needle shield 302 moves in the same downward direction, thereby compressing spring 604 as shown in FIG. 10. FIG. 11 shows a locking mechanism 1100 of needle-based device 100 in accordance with the embodiments of FIGS. 6 and 7, but as a variant thereof. Here, in one or more embodiments, locking mechanism 1100 may include a lock button 1102 (analogous to lock button 708) on needle shield 302 on a location proximate to end 114/top of needle mount 112; however, here, lock button 1102 may have a hook 1104 thereon configured to get between coils 1106 of spring 604 to touch the top of needle mount 112 and lock needle shield 302 by way of a hook tooth 1110 on hook 1104 catching onto one or more wire(s) of spring 604, as shown in FIG. 11; for the aforementioned purpose, needle shield 302 may have a groove 1108 on an outer wall thereof through which hook 1104 and hook tooth 1110 pass to lock into coils 1106 of spring 604 and the top of needle mount 112. This increases the lock force compared to the lock force in the embodiment of FIG. 7, where lock button 708 engages with external cap 702 instead.

Figure 12:
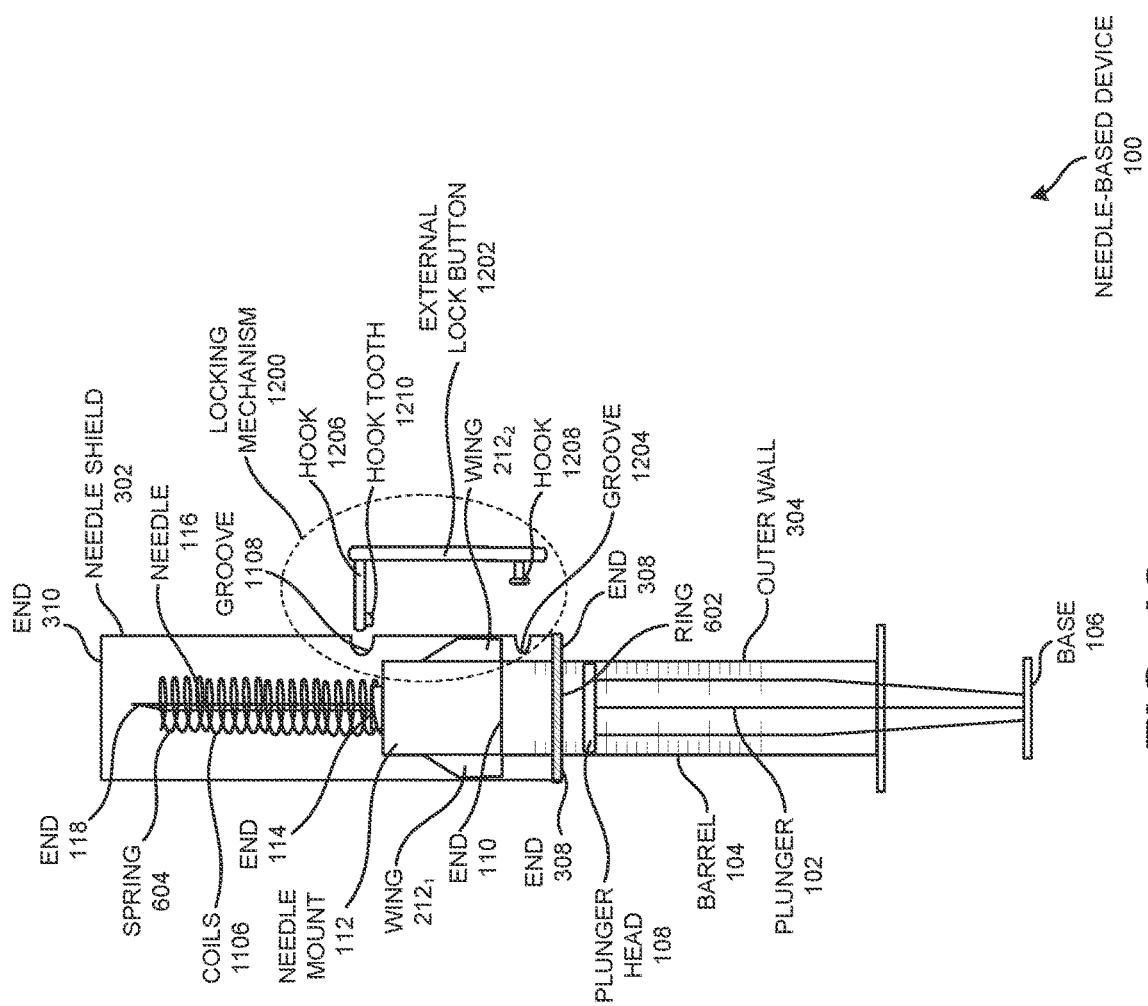
FIG. 12 is a schematic view of an external lock button utilized in the needle-based device of FIG. 6.

As discussed above, other possible embodiments include lock button 708 being a separate element that engages with needle shield 302 or both with needle shield 302 and spring 604. FIG. 12 shows an external lock button 1202 (e.g., part of locking mechanism 1200) that is configured to engage both with a groove 1204 on needle shield 302 (e.g., by way of a hook 1208 on external lock button 1202) and coils 1106 (e.g., through groove 1108 by way of another hook 1206 including a hook tooth 1210 on external lock button 1202) of spring 604. Again, the embodiment context of external lock button 1202 is similar to that of FIG. 6. In one or more embodiments, spring 604 discussed above may be a separate element or integrated with needle mount 112 discussed above or needle shield 302. In one or more embodiments, spring 604 may be a metal spring or molded spring. In one or more embodiments, needle shield 302 across all embodiments, along with other elements such as needle mount 112 and spring 604, may be sold as a safety mechanism distinct from a syringe or another form of needle-based device 100.

Figure 13:
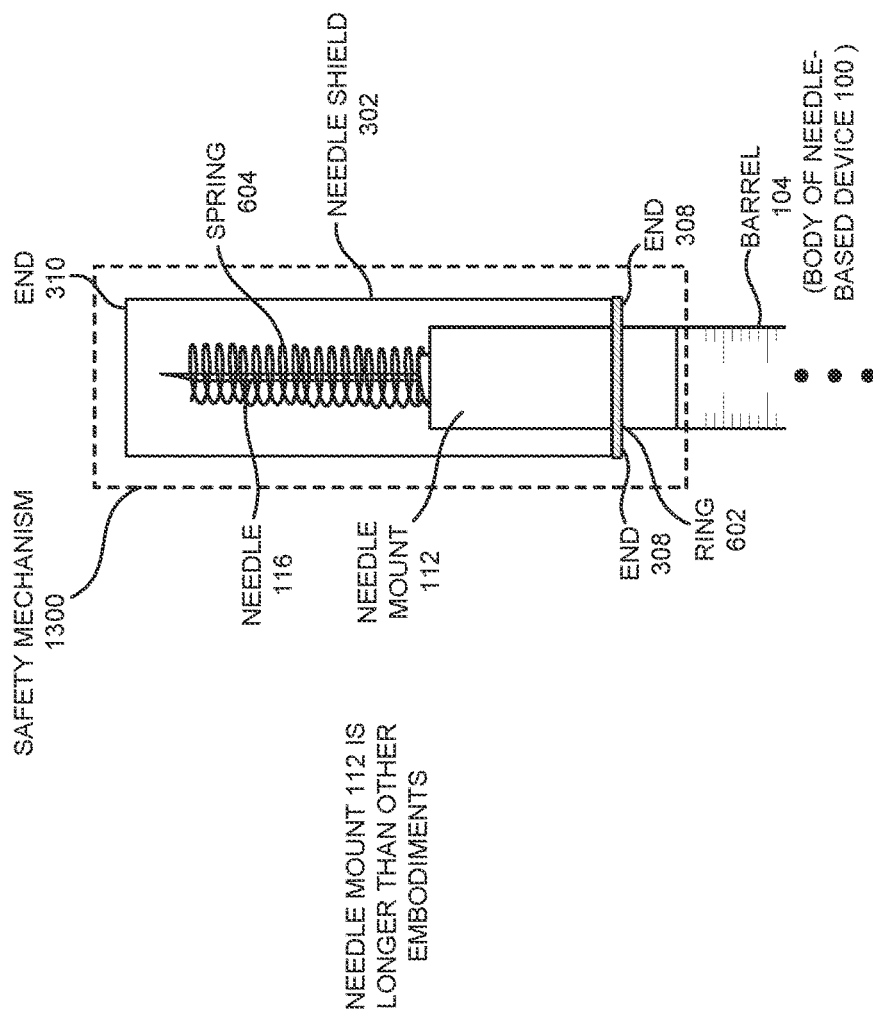
FIG. 13 is an illustrative view of a safety mechanism of the needle-based device of FIG. 6, with a longer needle mount.

FIG. 13 shows the embodiment of FIG. 6, but with a longer needle mount 112. Here, needle mount 112 may be longer such that ring 602 may be formed thereon instead of barrel 104. Thus, needle 116 with needle mount 112 and needle shield 302 may be sold as a separate safety mechanism 1300 distinct from needle based device 100. It should be noted that the manual embodiment of FIG. 3 also can include the lock mechanisms (e.g., those of FIG. 7 and FIGS. 11-12 (without catching wires of spring 604 as spring 604 does not exist in the embodiment of FIG. 3); it is easy to envision the embodiment of FIG. 7 without spring 604) discussed herein. All reasonable variations are within the scope of the exemplary embodiments discussed herein. Also, it should be noted that mechanisms of injection of a fluid into a body of a mammal and extraction of a fluid from a vial/bottle/body of the mammal are known to one skilled in the art, especially with regard to needle-based device 100. Detail discussion and illustration thereof are, therefore, skipped for the sake of convenience and clarity.

Embodiments of needle-based device 100 discussed above may further be modified to reduce complexity of assembly of components thereof and, thereby, not only render needle-based device 100 cost-effective and/or cost-competitive in the market but also provide increased value through needle-based device 100 to users (e.g., user 150) in terms of increased safety. It should be noted that plunger 102, as applicable to all embodiments discussed herein, may be provided with an element (e.g., rubber-based, rubber black) in the form of a stopper/gasket (not shown; e.g., attached to plunger head 108) to prevent fluid (e.g., medication) stored in barrel 104 from leaking when plunger 102 is pushed in or pulled out of a region within barrel 104.

Figure 14:
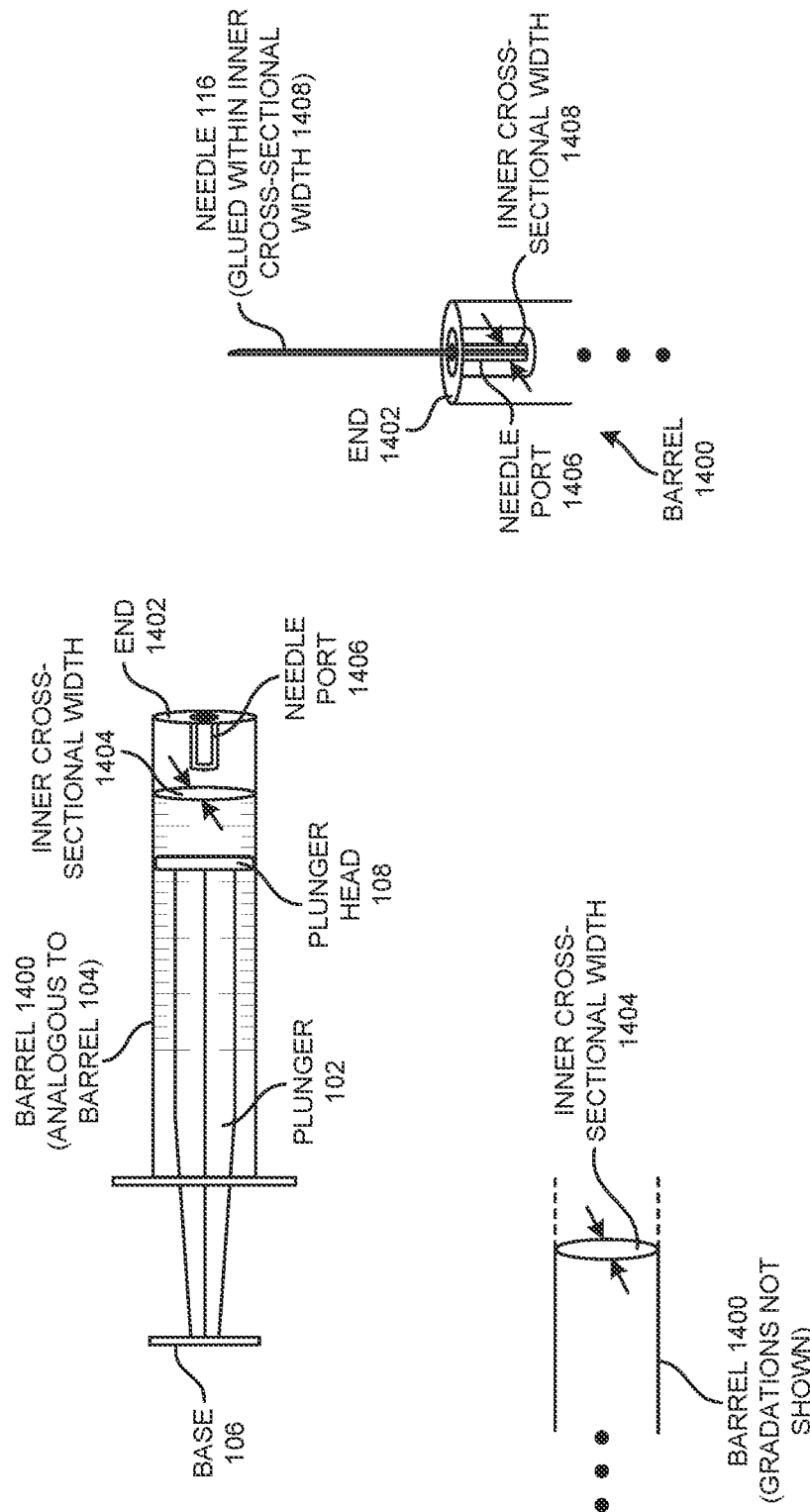
FIG. 14 is a schematic and an illustrative view of a barrel of a needle-based device analogous to a barrel of the needle-based device of FIGS. 1-13, according to one or more embodiments.

FIG. 14 shows barrel 1400 analogous to barrel 104 of the embodiments of FIGS. 1-13, according to one or more embodiments. Here, in one or more embodiments, a portion of barrel 1400 proximate an end 1402 thereof may include a needle port 1406 within an inner cross-sectional width 1404 (e.g., diameter) of barrel 1400. In one or more embodiments, needle port 1406 may be integrally formed with barrel 1400 and may be concentric with an outer wall (e.g., outer wall 1502, as will be discussed below) of barrel 1400. In one or more embodiments, needle port 1406 may extend from end 1402 into barrel 1400 within inner cross-sectional width 1404. In one or more embodiments, an inner cross-sectional width 1408 (e.g., diameter) of needle port 1406 may be significantly smaller than that of barrel 1400, i.e., inner cross-sectional width 1404. In one or more embodiments, needle 116 may have a portion thereof pass through needle port 1406 to be attached to barrel 1400. In other words, in one or more embodiments, the portion of needle 116 may be inserted into needle port 1406 and be attached thereinto in order for needle 116 to be attached to barrel 1400. Obviously, in one or more embodiments, a depth of needle port 1406 may be significantly lesser than a length of needle 116.

It should be noted that the cross-sectional width terminology has been employed herein instead of cross-sectional diameter in order to accommodate different shapes of barrel 1400 (barrel 104) and/or needle 116 such as cylinders and rectangular prisms. All possible shapes are within the scope of the exemplary embodiments discussed herein. Further, it should be noted that the extension of needle port 1406 from end 1402 into barrel 1400 within inner cross-sectional width 1404 thereof may cause needle port 1406 to be entirely encompassed within inner cross-sectional width 1404 of barrel 1400; here, an outer boundary of needle port 1406 along a length of barrel 1400 may at most be flush (or level) with an outer cross-sectional boundary of barrel 1400 at end 1402. In other words, needle port 1406 may be limited by end 1402 and may not protrude out of end 1402; at best, needle port 1406 may be flush with the outer cross-sectional boundary of barrel 1400 at end 1402.

In one or more embodiments, the attachment of needle 116 to barrel 1400 may be completed through gluing needle 116 to barrel 1400 within inner cross-sectional width 1408 of needle port 1406. FIG. 14 also shows a front view of the attachment of needle 116 to barrel 1400, according to one or more embodiments. In one or more embodiments, inner cross-sectional width 1408 of needle port 1406 may only be slightly higher than that of needle 116 to enable stable positioning of needle 116 therewithin. Here, in one or more embodiments, needle 116 may be glued within cross-sectional width 1408 of needle port 1406 to ensure said stable positioning thereof. In one example implementation, needle 116 may be glued within cross-sectional width 1408 of needle port 1406 of barrel 1400 using an Ultra-Violet (UV) resin. For example, needle 116 may be dipped in UV resin and inserted within needle port 1406 of a mold of barrel 1400 and cured (e.g., using a UV lamp) thereafter.

Figure 15:
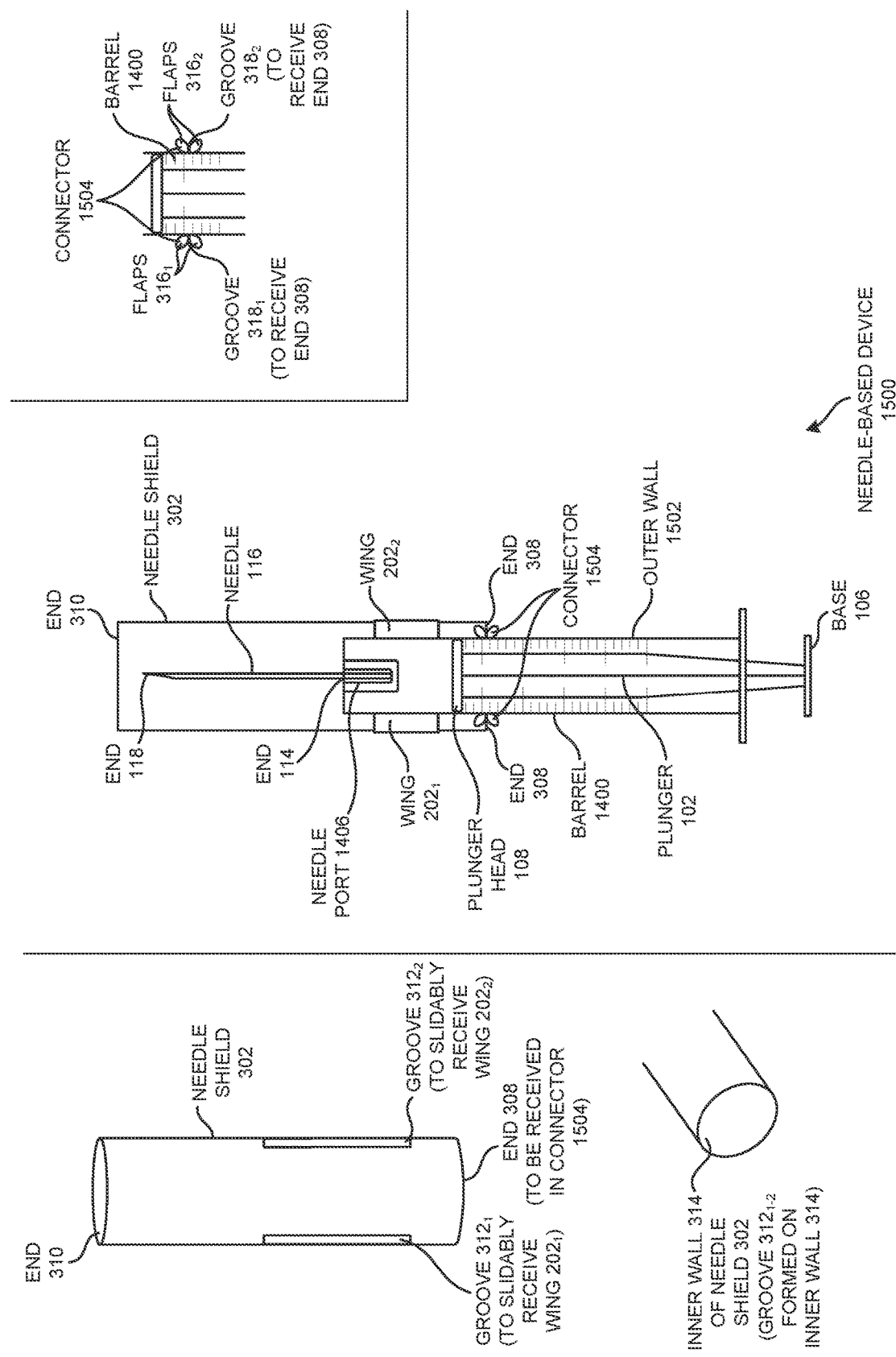
FIG. 15 is a schematic and an illustrative view of a needle-based device analogous to the needle-based device of FIGS. 1-13 with the barrel of FIG. 14 instead of the barrel of FIGS. 1-13, according to one or more embodiments.

All other possible methods (e.g., using epoxy resin) of stably connecting needle 116 within needle port 1406 are within the scope of the exemplary embodiments discussed herein. In one or more embodiments, the unstableness of needle 116 mounted on a conical structure/syringe cone may be avoided by the attachment of needle 116 to barrel 1400 discussed above. FIG. 15 shows a needle-based device 1500 analogous to needle-based device 100 with barrel 1400 instead of barrel 104, according to one or more embodiments. In one or more embodiments, the direct attachment of needle 116 to barrel 1400 instead of needle mount 112 as in needle-based device 100 may rid needle-based device 1500 of the need to have needle mount 112. In one or more embodiments, barrel 1400 may thus be accommodated with wings ($202_{1-2}$, $212_{1-2}$, $402_{1-2}$) on an outer wall 1502 thereof instead of wings ($202_{1-2}$, $212_{1-2}$, $402_{1-2}$) being provided on needle mount 112 in needle-based device 100. This was already discussed with respect to needle-based device 100 of FIG. 4.

FIG. 15 shows outer wall 1502 (analogous to outer wall 304) of barrel 1400 having a connector 1504 (analogous to connector 306) to enable end 308 of needle shield 302 discussed above to clasp onto connector 1504 while needle shield 302 completely encompasses needle 116 protruding from barrel 1400 (instead of needle mount 112 of needle-based device 100) of needle-based device 1500, according to one or more embodiments. It should be noted that the only difference between needle-based device 100 and needle-based device 1500 may be the absence of needle mount 112 and the direct attachment of needle 116 to barrel 1400 instead of needle mount 112. As discussed above, in one or more embodiments, the absence of needle mount 112 may enable accommodation of wings ($202_{1-2}$, $212_{1-2}$, $402_{1-2}$) on an outer surface (e.g., outer wall 1502) of barrel 1400. Thus, all mechanisms of coupling of needle shield 302 to barrel 104, the encompassing of needle 116 by needle shield 302, the mechanisms of working and coupling of spring 604/non-spring based embodiments of needle-based device 100, lock button (708, 1102, 1202), catching of coils of spring 604 by hook (1104, 1206) and the states of use and disuse of needle-based device 100 discussed above in addition to every relevant discussion are also applicable to needle-based device 1500 with barrel 1400 discussed herein.

In one or more embodiments, an inner cross-sectional dimension of needle shield 302 may be more than an outer cross-sectional dimension of barrel 1400 to enable the sliding of needle shield 302 over barrel 1400. In one or more embodiments, needle shield 302 may first receive the protruding needle 116 on barrel 1400 through end 308 thereof. In one or more embodiments, needle shield 302 may then be slid over barrel 1400 until end 308 clasps onto connector 1504 on outer wall 1502 of barrel 1400. In the state of needle shield 302 completely encompassing the protruding needle 116, the other end (e.g., end 310) of needle shield 302 may completely enclose end 118 of needle 116. FIG. 3 shows needle shield 302 to be transparent (e.g., needle shield 302 may be made of plastic, glass etc.). However, it should be noted that needle shield 302 may be translucent or opaque in certain embodiments. Similarly, barrel 1400 may be transparent, translucent or opaque in one or more embodiments.

In one or more embodiments, the outer wall of needle shield 302 may include cuts (not shown) that reveal needle 116 while needle 116 is still protected by needle shield 302. All reasonable variations are within the scope of the exemplary embodiments discussed herein. In one or more embodiments, the sliding of needle shield 302 over barrel 1400 may be facilitated by wings $202_{1-2}$ now provided on outer wall 1502 of barrel 1400 instead of on needle mount 112. Again, analogous to FIG. 3, for the aforementioned purpose, optionally, grooves $312_{1-2}$ may be provided on an inner wall 314 of needle shield 302. In one or more embodiments, wings $202_{1-2}$ of barrel 1400 may be received within grooves $312_{1-2}$ during relative sliding of wings $202_{1-2}$ with respect to grooves $312_{1-2}$. While FIG. 15 again shows grooves $312_{1-2}$ as cutting across inner wall 314 of needle shield 302 into an entire thickness thereof, it should be noted that grooves $312_{1-2}$ may not cut across inner wall 314 of needle shield 302 completely in one or more alternative embodiments. In one or more embodiments, needle shield 302 may slide until reception thereof within connector 1504. In one or more embodiments, connector 1504 may be constituted by flexible pairs of flaps $316_{1-2}$, each forming a groove $318_{1-2}$ to receive end 308 of needle shield 302 therewithin.

It should be noted that, while FIG. 4 shows wings (e.g., wings $402_{1-2}$) on lateral sides of barrel 104, FIG. 15 additionally includes needle 116 directly attached to barrel 1400 as discussed above without the need for needle mount 112 therefor. It is easy to envision the needle-based device 100 embodiment of FIG. 5 being applied to needle-based device 1500 with barrel 1400 instead of barrel 104. In one or more embodiments, ring 502 may be provided on outer wall 1502 of barrel 1400 and needle 116 may be directly attached to barrel 1400. The protrusion of ring 502 from outer wall 1502 of barrel 1400, groove 504 on the underside of ring 502 complementary to the protrusion 506 on end 308 of needle shield 302, the locking of protrusion 506 of needle shield 302 onto groove 504 of ring 502 following movement of needle shield 302 toward barrel 1400 to enable needle shield 302 to completely encompass the protruding needle 116 therewithin and other features/discussions pertaining to FIG. 5 are also applicable to needle-based device 1500 discussed throughout.

Figure 16:
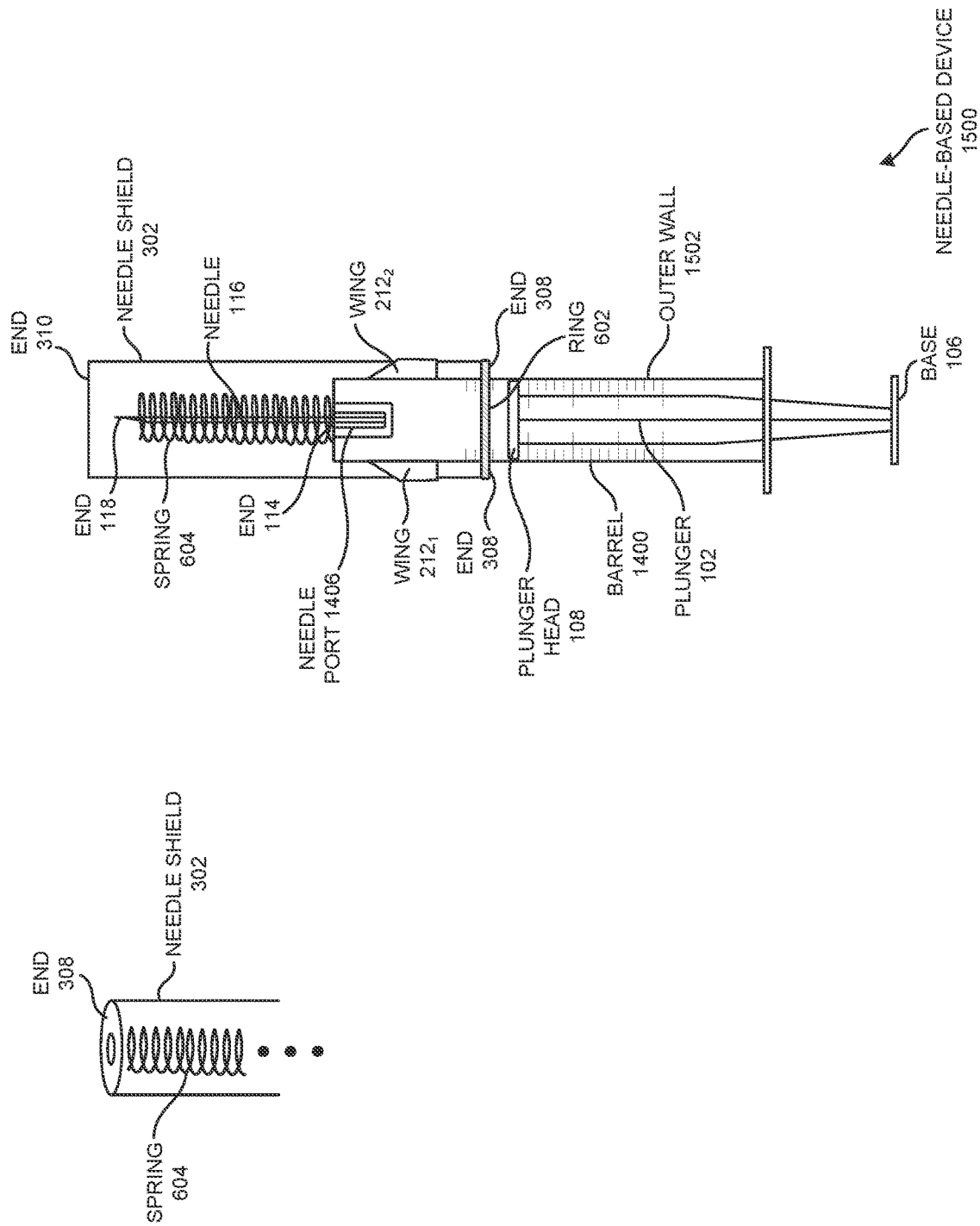
FIG. 16 is a schematic and an illustrative view of the needle-based device of FIG. 15 with a spring analogous to the spring of the needle-based device of FIG. 6 encompassing a needle in a state of disuse thereof, according to one or more embodiments.

FIG. 16 shows needle-based device 1500 with barrel 1400 with spring 604 encompassing needle 116 in a state of disuse thereof, according to one or more embodiments. Here, in one or more embodiments, barrel 1400 may include wings $212_{1-2}$ on outer wall 1502 thereof. The working of spring 604 and compression thereof to enable needle 116 to emerge out of needle shield 302 and other concepts/discussions pertaining to all embodiments relevant to the implementation of spring 604 in needle-based device 100 may also be applicable to needle-based device 1500. For example, it should be noted that, instead of spring 604 resting on needle mount 112 to additionally encompass the entire protruding length of needle 116 in the first state of disuse of needle-based device 100 as in FIG. 6, spring 604 may rest on barrel 1400 in the first state of disuse of needle-based device 1500 as in FIG. 16.

Figure 17:
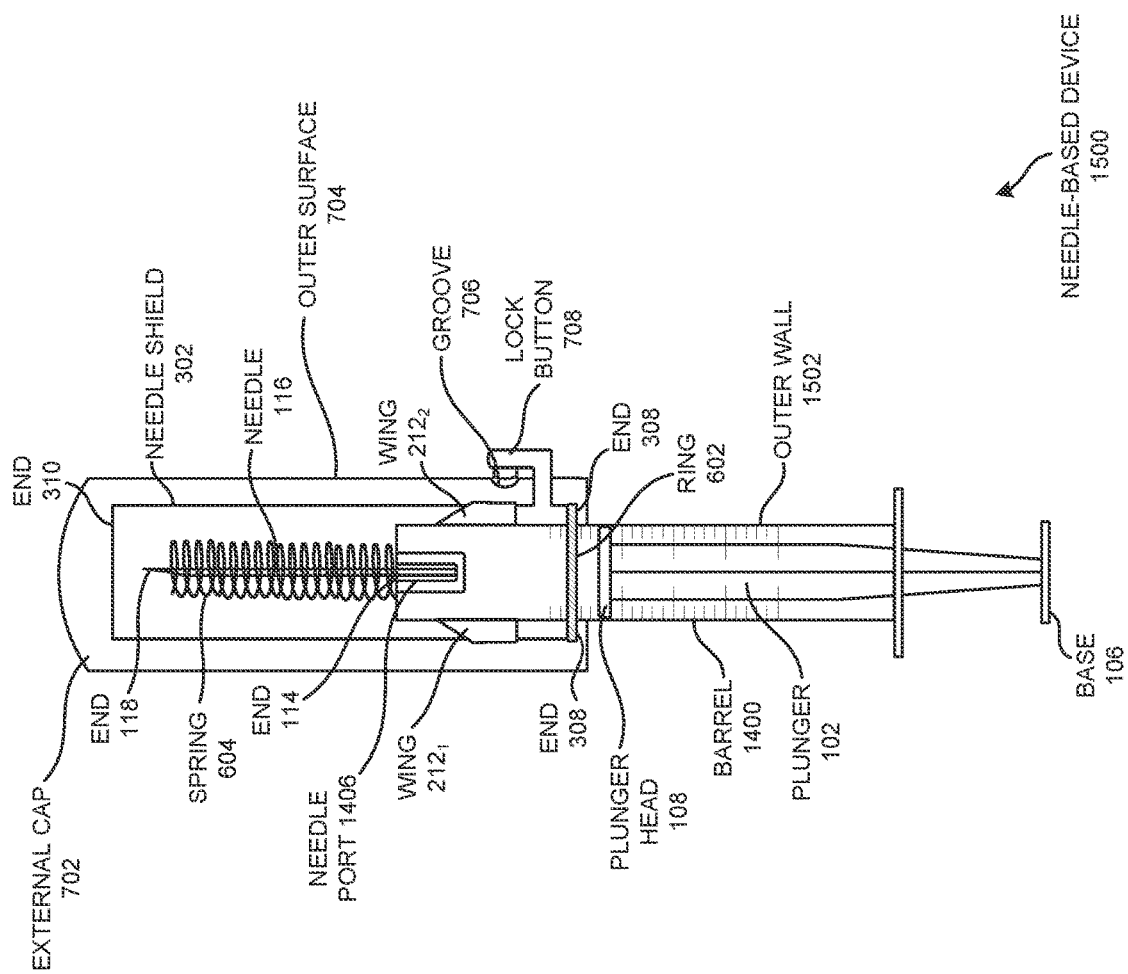
FIG. 17 is a schematic and an illustrative view of the needle-based device of FIGS. 15-16 with a lock button and the external cap of the needle-based device of FIG. 7, according to one or more embodiments.
Figure 18:
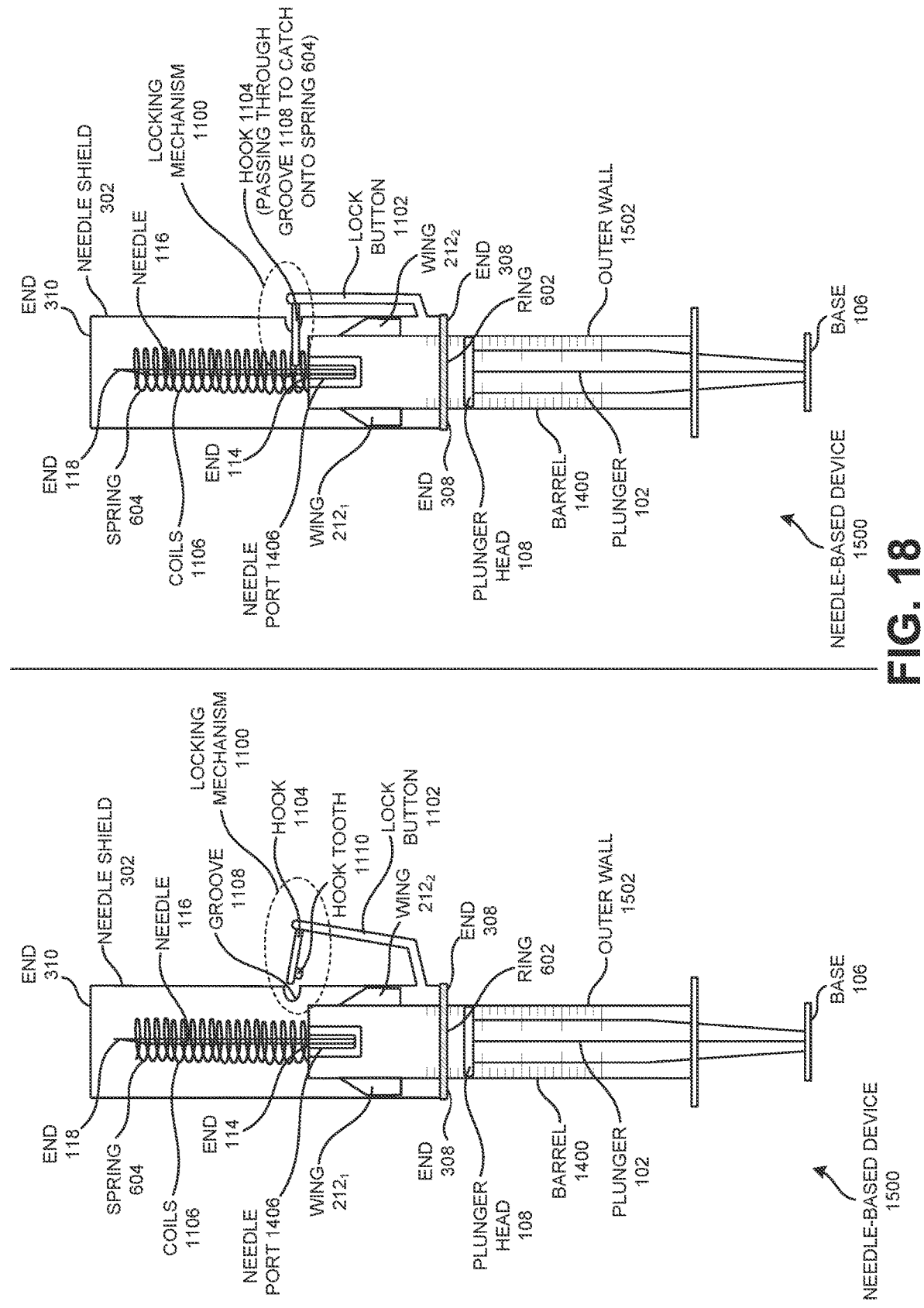
FIG. 18 is a schematic and an illustrative view of the needle-based device of FIGS. 15-16 with a lock button of the needle-based device of FIG. 11, according to one or more embodiments.
Figure 19:
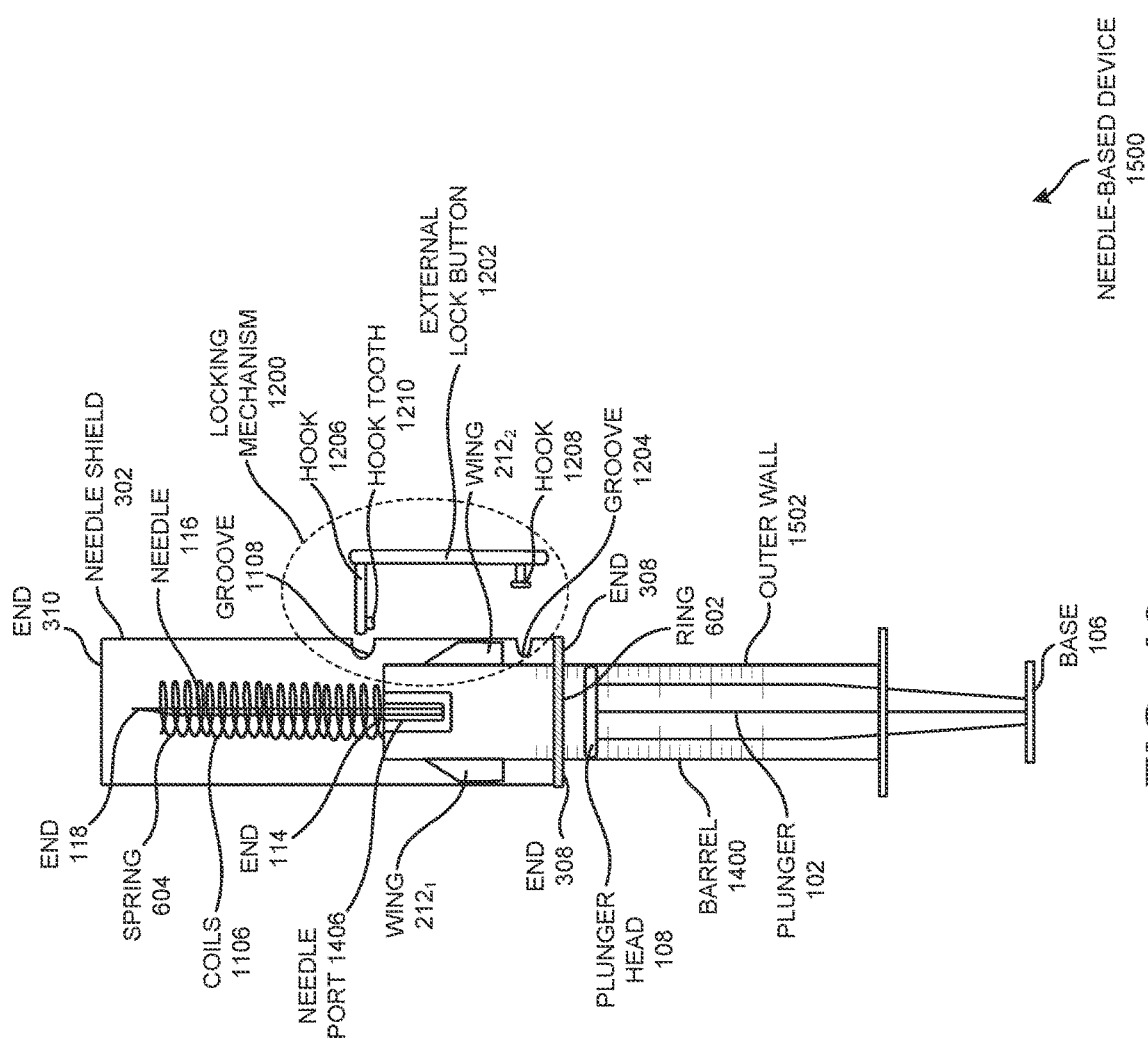
FIG. 19 is a schematic and an illustrative view of the needle-based device of FIGS. 15-16 with an external lock button and a corresponding groove on a needle shield thereof analogous to the embodiment of FIG. 12, according to one or more embodiments.

FIG. 17 shows needle-based device 1500 in the same context as needle-based device 100 of FIG. 7 with lock button 708 and external cap 702, according to one or more embodiments. FIG. 18 shows needle-based device 1500 in the same context as needle-based device 100 with lock button 1102 on needle shield 302, according to one or more embodiments. Similarly, FIG. 19 shows needle-based device 1500 in the same context as needle-based device 100 with external lock button 1202 and corresponding groove 1204 on needle shield 302, according to one or more embodiments.

As the only difference between the embodiments of needle-based device 100 of FIGS. 1-13 and the embodiments of needle-based device 1500 with barrel 1400 of the subsequent figures lie in needle 116 being directly attached/glued to barrel 1400 and wings ($202_{1-2}$, $212_{1-2}$, $402_{1-2}$) being provided on outer wall 1502 of barrel 1400 instead of on needle mount 112, detailed explanations pertaining to the working of needle-based device 1500 have been skipped for the sake of convenience, clarity, brevity and avoiding repetition. All functional and structural elements of the embodiments of needle-based device 100 of FIGS. 1-13 and the states of use and disuse thereof are also applicable to the embodiments of needle-based device 1500 of the subsequent figures. All reasonable variations are within the scope of the exemplary embodiments discussed herein.

Thus, exemplary embodiments discussed with reference to FIGS. 14-19 may eliminate the need for needle mount 112 of the embodiments of needle-based device 100 of FIGS. 1-13. In one or more embodiments, the attaching of needle 116 directly to barrel 1400 and the provision of wings ($202_{1-2}$, $212_{1-2}$, $402_{1-2}$) directly on barrel 1400 render the injection mold of barrel 1400 to offer more components thereon. This may reduce the need for an entity manufacturing barrel 1400 to seek components such as needle mount 112 from third-party entities. Further, this may reduce the costs of needle-based device 1500 based on the efficiency involved in a one-stop manufacturing process and/or a reduced number of components compared to needle-based device 100 of FIGS. 1-13. All reasonable variations are within the scope of the exemplary embodiments discussed herein.

Although the present embodiments have been described with reference to specific example embodiments, it will be evident that various modifications and changes may be made to these embodiments without departing from the broader spirit and scope of the various embodiments. Accordingly, the specification and drawings are to be regarded in an illustrative rather than a restrictive sense.

What is claimed is:

1. A needle-based device comprising:
    a barrel as a body of the needle-based device;
    a needle, a portion of which is received within the barrel and glued thereinto to cause the needle to protrude from the barrel;
    a needle shield to protect an entire length of the needle protruding from the barrel based on completely encompassing the entire protruding length of the needle in a first state of disuse of the needle-based device; and
    a lock button with a first end, the first end is either integrally formed with the needle shield or external to the needle shield and then coupled to the needle shield, and a length of the lock button is completely external to the needle shield, wherein the needle shield is locked with the lock button in the first state of disuse of the needle-based device based on:
the lock button comprising a hook at a second end thereof that passes through a groove formed on the needle shield such that, during the locking of the needle shield:
the length of the lock button completely external to the needle shield is parallel to a length of the needle shield and the entire protruding length of the needle, and
the hook is perpendicular to the length of the needle shield, the length of the lock button and the entire protruding length of the needle, and
wherein the barrel comprises wings on lateral sides of an outer wall thereof, the wings extending perpendicular to a length of the barrel to couple the needle shield to the barrel in the first state of disuse of the needle-based device.

2. The needle-based device of claim 1, wherein:
the barrel comprises a needle port proximate an end thereof integrally formed with the barrel, the needle port being within an inner cross-sectional width of the barrel and concentric with the outer wall of the barrel, and the needle port extending from the end of the barrel thereinto within the inner cross-sectional width of the barrel such that the needle port is entirely encompassed within the inner cross-sectional width of the barrel and an outer boundary of the needle port along the length of the barrel is at most flush with an outer cross-sectional boundary of the barrel at the end of the barrel, and
the portion of the needle is received within an inner cross-sectional width of the needle port and glued thereinto.

3. The needle-based device of claim 2, wherein the portion of the needle is glued into the inner cross-sectional width of the needle port using an Ultra-Violet (UV) resin.

4. The needle-based device of claim 1, wherein:
the needle shield is retracted in a first direction toward the barrel to apply a first force in the first direction to cause the needle to emerge out of the needle shield to prepare the needle-based device for a second state of use thereof,
the needle-based device is transitioned back to the first state of disuse thereof following the second state of use in accordance with applying a second force in a second direction diametrically opposite to the first direction, and
the encompassing of the entire protruding length of the needle by the needle shield in the first state of disuse of the needle-based device is securely maintained based on the coupling of the needle shield to the barrel via the wings.

5. The needle-based device of claim 1, further comprising a spring resting on the barrel to additionally encompass the entire protruding length of the needle in the first state of disuse of the needle-based device.

6. The needle-based device of claim 5,
wherein the needle shield encompasses an entire length of the spring in addition to the entire protruding length of the needle in the first state of disuse of the needle-based device.

7. The needle-based device of claim 6, wherein:
the needle shield is retracted in a first direction toward the barrel to compress the spring that applies a first force in the first direction to cause the needle to emerge out of the needle shield to prepare the needle-based device for a second state of use thereof, and
the needle-based device is automatically transitioned back to the first state of disuse thereof immediately following the second state of use in accordance with automatic decompression of the spring that provides for a second force in a second direction diametrically opposite to the first direction.

8. A needle-based device comprising:
a barrel as a body of the needle-based device, the barrel comprising a needle port proximate an end thereof integrally formed with the barrel, the needle port being within an inner cross-sectional width of the barrel and concentric with an outer wall of the barrel, and the needle port extending from the end of the barrel thereinto within the inner cross-sectional width of the barrel such that the needle port is entirely encompassed within the inner cross-sectional width of the barrel and an outer boundary of the needle port along a length of the barrel is at most flush with an outer cross-sectional boundary of the barrel at the end of the barrel;
a needle, a portion of which is received within an inner cross-sectional width of the needle port and glued thereinto to cause the needle to protrude from the barrel;
a needle shield to protect an entire length of the needle protruding from the barrel based on completely encompassing the entire protruding length of the needle in a first state of disuse of the needle-based device; and
a lock button with a first end, the first end is either integrally formed with the needle shield or external to the needle shield and then coupled to the needle shield, and a length of the lock button is completely external to the needle shield,
wherein the needle shield is locked with the lock button in the first state of disuse of the needle-based device based on:
the lock button comprising a hook at a second end thereof that passes through a groove formed on the needle shield such that, during the locking of the needle shield:
the length of the lock button completely external to the needle shield is parallel to a length of the needle shield and the entire protruding length of the needle, and
the hook is perpendicular to the length of the needle shield, the length of the lock button and the entire protruding length of the needle, and
wherein the barrel comprises wings on lateral sides of the outer wall thereof, the wings extending perpendicular to the length of the barrel to couple the needle shield to the barrel in the first state of disuse of the needle-based device.

9. The needle-based device of claim 8, wherein:
the needle shield is retracted in a first direction toward the barrel to apply a first force in the first direction to cause the needle to emerge out of the needle shield to prepare the needle-based device for a second state of use thereof,
the needle-based device is transitioned back to the first state of disuse thereof following the second state of use in accordance with applying a second force in a second direction diametrically opposite to the first direction, and
the encompassing of the entire protruding length of the needle by the needle shield in the first state of disuse of the needle-based device is securely maintained based on the coupling of the needle shield to the barrel via the wings.

10. The needle-based device of claim 8, further comprising a spring resting on the barrel to additionally encompass the entire protruding length of the needle in the first state of disuse of the needle-based device.

11. The needle-based device of claim 10,
wherein the needle shield encompasses an entire length of the spring in addition to the entire protruding length of the needle in the first state of disuse of the needle-based device.

12. The needle-based device of claim 11, wherein:
the needle shield is retracted in a first direction toward the barrel to compress the spring that applies a first force in the first direction to cause the needle to emerge out of the needle shield to prepare the needle-based device for a second state of use thereof, and
the needle-based device is automatically transitioned back to the first state of disuse thereof immediately following the second state of use in accordance with automatic decompression of the spring that provides for a second force in a second direction diametrically opposite to the first direction.

13. The needle-based device of claim 8, wherein the portion of the needle is glued into the inner cross-sectional width of the needle port using a UV resin.

14. A needle-based device comprising:
a barrel as a body of the needle-based device;
a needle, a portion of which is received within the barrel and glued thereinto to cause the needle to protrude from the barrel;
a needle shield to protect an entire length of the needle protruding from the barrel based on completely encompassing the entire protruding length of the needle in a first state of disuse of the needle-based device; and
a lock button with a first end, the first end is either integrally formed with the needle shield or external to the needle shield and then coupled to the needle shield, and a length of the lock button is completely external to the needle shield,
wherein the needle shield is locked with the lock button in the first state of disuse of the needle-based device based on:
the lock button comprising a hook at a second end thereof that passes through a groove formed on the needle shield such that, during the locking of the needle shield:
the length of the lock button completely external to the needle shield is parallel to a length of the needle shield and the entire protruding length of the needle, and
the hook is perpendicular to the length of the needle shield, the length of the lock button and the entire protruding length of the needle,
wherein the barrel comprises wings on lateral sides of an outer wall thereof, the wings extending perpendicular to a length of the barrel to couple the needle shield to the barrel in the first state of disuse of the needle-based device, and wherein the needle shield is retracted in a first direction toward the barrel to apply a first force in the first direction to cause the needle to emerge out of the needle shield to prepare the needle-based device for a second state of use thereof.

15. The needle-based device of claim 14, wherein:
the barrel comprises a needle port proximate an end thereof integrally formed with the barrel, the needle port being within an inner cross-sectional width of the barrel and concentric with the outer wall of the barrel, and the needle port extending from the end of the barrel thereinto within the inner cross-sectional width of the barrel such that the needle port is entirely encompassed within the inner cross-sectional width of the barrel and an outer boundary of the needle port along the length of the barrel is at most flush with an outer cross-sectional boundary of the barrel at the end of the barrel, and
the portion of the needle is received within an inner cross-sectional width of the needle port and glued thereinto.

16. The needle-based device of claim 15, wherein the portion of the needle is glued into the inner cross-sectional width of the needle port using a UV resin.

17. The needle-based device of claim 14, wherein:
the needle-based device is transitioned back to the first state of disuse thereof following the second state of use in accordance with applying a second force in a second direction diametrically opposite to the first direction, and
the encompassing of the entire protruding length of the needle by the needle shield in the first state of disuse of the needle-based device is securedly maintained based on the coupling of the needle shield to the barrel via the wings.

18. The needle-based device of claim 14, further comprising a spring resting on the barrel to additionally encompass the entire protruding length of the needle in the first state of disuse of the needle-based device,
wherein the needle shield encompasses an entire length of the spring in addition to the entire protruding length of the needle in the first state of disuse of the needle-based device.

19. The needle-based device of claim 18, wherein:
the needle shield is retracted in the first direction toward the barrel to compress the spring that applies the first force in the first direction to cause the needle to emerge out of the needle shield to prepare the needle-based device for the second state of use thereof, and
the needle-based device is automatically transitioned back to the first state of disuse thereof immediately following the second state of use in accordance with automatic decompression of the spring that provides for a second force in a second direction diametrically opposite to the first direction.

20. The needle-based device of claim 19, wherein the encompassing of the entire protruding length of the needle and the encompassing of the entire protruding length of the spring by the needle shield in the first state of disuse of the needle-based device are securedly maintained based on the coupling of the needle shield to the barrel via the wings.

* * * * *